US009039617B2

(12) United States Patent
Slayton et al.

(10) Patent No.: US 9,039,617 B2
(45) Date of Patent: *May 26, 2015

(54) METHODS AND SYSTEMS FOR GENERATING THERMAL BUBBLES FOR IMPROVED ULTRASOUND IMAGING AND THERAPY

(71) Applicant: Guided Therapy Systems, LLC, Mesa, AZ (US)

(72) Inventors: Michael H. Slayton, Phoenix, AZ (US); Peter G. Barthe, Phoenix, AZ (US); Inder Raj S. Makin, Mesa, AZ (US)

(73) Assignee: Guided Therapy Systems, LLC, Mesa, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/270,859

(22) Filed: May 6, 2014

(65) Prior Publication Data
US 2014/0243713 A1 Aug. 28, 2014

Related U.S. Application Data

(63) Continuation of application No. 12/954,484, filed on Nov. 24, 2010, now Pat. No. 8,715,186.

(60) Provisional application No. 61/263,916, filed on Nov. 24, 2009.

(51) Int. Cl.
*A61B 8/00* (2006.01)
*A61N 7/00* (2006.01)
(Continued)

(52) U.S. Cl.
CPC ............... *A61N 7/00* (2013.01); *A61B 8/4472* (2013.01); *A61B 8/48* (2013.01);
(Continued)

(58) Field of Classification Search
USPC ............................ 600/437, 439, 441; 601/2
See application file for complete search history.

(56) References Cited

U.S. PATENT DOCUMENTS 2,427,348 A 9/1947 Bond et al.
3,913,386 A 10/1975 Saglio
(Continued)

FOREIGN PATENT DOCUMENTS

DE 4029175 3/1992
DE 10140064 3/2003
(Continued)

OTHER PUBLICATIONS

Sassen, Sander, "ATI's R520 architecture, the new king of the hill?" http://www.hardwareanalysis.com/content/article/1813, Sep. 16, 2005, 2 pages.
(Continued)

*Primary Examiner* — Unsu Jung
*Assistant Examiner* — Joel Lamprecht
(74) *Attorney, Agent, or Firm* — Quarles & Brady, LLP

(57) ABSTRACT

A method and system uniquely capable of generating thermal bubbles for improved ultrasound imaging and therapy. Several embodiments of the method and system contemplates the use of unfocused, focused, or defocused acoustic energy at variable spatial and/or temporal energy settings, in the range of about 1 kHz-100 MHz, and at variable tissue depths. The unique ability to customize acoustic energy output and target a particular region of interest makes possible highly accurate and precise thermal bubble formation. In an embodiment, the energy is acoustic energy. In other embodiments, the energy is photon based energy (e.g., IPL, LED, laser, white light, etc.), or other energy forms, such radio frequency electric currents (including monopolar and bipolar radio-frequency current). In an embodiment, the energy is various combinations of acoustic energy, electromagnetic energy and other energy forms or energy absorbers such as cooling.

19 Claims, 11 Drawing Sheets

(51) Int. Cl.
*A61B 8/08* (2006.01)
*A61B 18/00* (2006.01)

(52) U.S. Cl.
CPC ............. *A61B 2018/00642* (2013.01); *A61N 2007/0039* (2013.01); *A61N 2007/0056* (2013.01); *A61N 2007/006* (2013.01); *A61N 2007/0065* (2013.01); *A61N 2007/0073* (2013.01)

(56) References Cited

U.S. PATENT DOCUMENTS

| | | |
|---|---|---|
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,166,967 A | 9/1979 | Benes et al. |
| 4,211,948 A | 7/1980 | Brisken et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Tanezer |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller et al. |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough et al. |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry et al. |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh et al. |
| 4,917,096 A | 4/1990 | Englehart |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry et al. |
| 4,955,365 A | 9/1990 | Fry et al. |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry et al. |
| 5,040,537 A | 8/1991 | Katakura |
| 5,054,310 A | 10/1991 | Flynn |
| 5,054,470 A | 10/1991 | Fry et al. |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi et al. |
| 5,123,418 A | 6/1992 | Saurel |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D'Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada et al. |
| 5,269,297 A | 12/1993 | Weng |
| 5,282,797 A | 2/1994 | Chess |
| 5,295,484 A | 3/1994 | Marcus et al. |
| 5,295,486 A | 3/1994 | Wollschlaeger et al. |
| 5,304,169 A | 4/1994 | Sand |
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,348,016 A | 9/1994 | Unger et al. |
| 5,360,268 A | 11/1994 | Hayashi |
| 5,370,121 A | 12/1994 | Reichenberger et al. |
| 5,371,483 A | 12/1994 | Bhardwaj |
| 5,375,602 A | 12/1994 | Lancee et al. |
| 5,379,773 A | 1/1995 | Hornsby |
| 5,380,280 A | 1/1995 | Peterson |
| 5,380,519 A | 1/1995 | Schneider et al. |
| 5,383,917 A | 1/1995 | Desai et al. |
| 5,391,140 A | 2/1995 | Schaetzle et al. |
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams, Jr. et al. |
| 5,417,216 A | 5/1995 | Tanaka |
| 5,419,327 A | 5/1995 | Rohwedder |
| 5,423,220 A | 6/1995 | Finsterwald et al. |
| 5,435,311 A | 7/1995 | Umemura et al. |
| 5,438,998 A | 8/1995 | Hanafy |
| 5,458,596 A | 10/1995 | Lax |
| 5,460,179 A | 10/1995 | Okunuki et al. |
| 5,460,595 A | 10/1995 | Hall et al. |

(56) References Cited

U.S. PATENT DOCUMENTS

| | | |
|---|---|---|
| 5,469,854 A | 11/1995 | Unger et al. |
| 5,471,988 A | 12/1995 | Fujio |
| 5,487,388 A | 1/1996 | Rello et al. |
| 5,492,126 A | 2/1996 | Hennige et al. |
| 5,496,256 A | 3/1996 | Bock |
| 5,501,655 A | 3/1996 | Rolt et al. |
| 5,503,152 A | 4/1996 | Oakley et al. |
| 5,503,320 A | 4/1996 | Webster et al. |
| 5,507,790 A | 4/1996 | Weiss |
| 5,520,188 A | 5/1996 | Hennige et al. |
| 5,522,869 A | 6/1996 | Burdette et al. |
| 5,523,058 A | 6/1996 | Umemura et al. |
| 5,524,620 A | 6/1996 | Rosenschein |
| 5,524,624 A | 6/1996 | Tepper |
| 5,524,625 A | 6/1996 | Okazaki et al. |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz et al. |
| 5,529,070 A | 6/1996 | Augustine et al. |
| 5,540,235 A | 7/1996 | Wilson |
| 5,558,092 A | 9/1996 | Unger et al. |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,601,526 A | 2/1997 | Chapelon et al. |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,622,175 A | 4/1997 | Sudol et al. |
| 5,638,819 A | 6/1997 | Manwaring et al. |
| 5,643,179 A | 7/1997 | Fujimoto |
| 5,644,085 A | 7/1997 | Lorraine et al. |
| 5,647,373 A | 7/1997 | Paltieli |
| 5,655,535 A | 8/1997 | Friemel et al. |
| 5,655,538 A | 8/1997 | Lorraine |
| 5,657,760 A | 8/1997 | Ying et al. |
| 5,658,328 A | 8/1997 | Johnson |
| 5,660,836 A | 8/1997 | Knowlton |
| 5,662,116 A | 9/1997 | Kondo et al. |
| 5,665,053 A | 9/1997 | Jacobs |
| 5,665,141 A | 9/1997 | Vago |
| 5,671,746 A | 9/1997 | Dreschel et al. |
| 5,673,699 A | 10/1997 | Trahey et al. |
| 5,676,692 A | 10/1997 | Sanghvi et al. |
| 5,685,820 A | 11/1997 | Riek et al. |
| 5,687,737 A | 11/1997 | Branham et al. |
| 5,690,608 A | 11/1997 | Watanabe |
| 5,694,936 A | 12/1997 | Fujimoto et al. |
| 5,697,897 A | 12/1997 | Buchholtz et al. |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki et al. |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law et al. |
| 5,763,886 A | 6/1998 | Schulte |
| 5,769,790 A | 6/1998 | Watkins et al. |
| 5,779,644 A | 7/1998 | Eberle et al. |
| 5,792,058 A | 8/1998 | Lee et al. |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle et al. |
| 5,827,204 A | 10/1998 | Grandia et al. |
| 5,839,751 A | 11/1998 | Bonin |
| 5,840,032 A | 11/1998 | Hatfield et al. |
| 5,844,140 A | 12/1998 | Seale |
| 5,853,367 A | 12/1998 | Chalek et al. |
| 5,869,751 A | 2/1999 | Bonin |
| 5,871,524 A | 2/1999 | Knowlton |
| 5,873,902 A | 2/1999 | Sanghvi et al. |
| 5,876,431 A | 3/1999 | Spehr et al. |
| 5,879,303 A | 3/1999 | Averkiou et al. |
| 5,882,557 A | 3/1999 | Hayakawa |
| 5,891,034 A | 4/1999 | Bucholz |
| 5,899,861 A | 5/1999 | Friemel et al. |
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schaetzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,967,980 A | 10/1999 | Ferre et al. |
| 5,968,034 A | 10/1999 | Fulmer |
| 5,971,949 A | 10/1999 | Levin |
| 5,977,538 A | 11/1999 | Unger et al. |
| 5,984,882 A | 11/1999 | Rosenschein et al. |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,016,255 A | 1/2000 | Bolan et al. |
| 6,019,724 A | 2/2000 | Gronningsaeter et al. |
| 6,022,308 A | 2/2000 | Williams |
| 6,022,327 A | 2/2000 | Chang |
| 6,036,646 A | 3/2000 | Barthe |
| 6,039,048 A | 3/2000 | Silberg |
| 6,039,689 A | 3/2000 | Lizzi |
| 6,042,556 A | 3/2000 | Beach et al. |
| 6,049,159 A | 4/2000 | Barthe |
| 6,050,943 A | 4/2000 | Slayton et al. |
| 6,059,727 A | 5/2000 | Fowlkes |
| 6,071,239 A | 6/2000 | Cribbs et al. |
| 6,080,108 A | 6/2000 | Dunham |
| 6,083,148 A | 7/2000 | Williams |
| 6,086,535 A | 7/2000 | Ishibashi et al. |
| 6,086,580 A | 7/2000 | Mordon et al. |
| 6,090,054 A | 7/2000 | Tagishi |
| 6,093,883 A | 7/2000 | Sanghvi |
| 6,101,407 A | 8/2000 | Groezinger |
| 6,106,469 A | 8/2000 | Suzuki et al. |
| 6,113,558 A | 9/2000 | Rosenschein et al. |
| 6,113,559 A | 9/2000 | Klopotek |
| 6,120,452 A | 9/2000 | Barthe |
| 6,123,081 A | 9/2000 | Durette |
| 6,126,619 A | 10/2000 | Peterson et al. |
| 6,135,971 A | 10/2000 | Hutchinson et al. |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |

(56) References Cited

U.S. PATENT DOCUMENTS

| | | |
|---|---|---|
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Digs |
| 6,190,336 B1 | 2/2001 | Duarte |
| 6,193,658 B1 | 2/2001 | Wendelken et al. |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao |
| 6,273,864 B1 | 8/2001 | Duarte |
| 6,280,402 B1 | 8/2001 | Ishibashi et al. |
| 6,287,257 B1 | 9/2001 | Matichuk |
| 6,296,619 B1 | 10/2001 | Brisken |
| 6,301,989 B1 | 10/2001 | Brown et al. |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,758 B1 | 12/2001 | Carol et al. |
| 6,325,769 B1 | 12/2001 | Klopotek |
| 6,325,798 B1 | 12/2001 | Edwards et al. |
| 6,338,716 B1 | 1/2002 | Hossack et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 | 7/2002 | Cain et al. |
| 6,413,253 B1 | 7/2002 | Koop |
| 6,413,254 B1 | 7/2002 | Hissong |
| 6,419,648 B1 | 7/2002 | Vitek |
| 6,423,007 B2 | 7/2002 | Lizzi et al. |
| 6,425,865 B1 | 7/2002 | Salcudean |
| 6,425,867 B1 | 7/2002 | Vaezy et al. |
| 6,425,912 B1 | 7/2002 | Knowlton |
| 6,428,477 B1 | 8/2002 | Mason |
| 6,428,532 B1 | 8/2002 | Doukas |
| 6,430,446 B1 | 8/2002 | Knowlton |
| 6,432,057 B1 | 8/2002 | Mazess et al. |
| 6,432,067 B1 | 8/2002 | Martin et al. |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Costantino |
| 6,453,202 B1 | 9/2002 | Knowlton |
| 6,461,378 B1 | 10/2002 | Knowlton |
| 6,470,216 B1 | 10/2002 | Knowlton |
| 6,488,626 B1 | 12/2002 | Lizzi et al. |
| 6,491,657 B2 | 12/2002 | Rowe |
| 6,500,121 B1 | 12/2002 | Slayton |
| 6,500,141 B1 | 12/2002 | Irion |
| 6,508,774 B1 | 1/2003 | Acker et al. |
| 6,511,427 B1 | 1/2003 | Sliwa, Jr. et al. |
| 6,511,428 B1 | 1/2003 | Azuma |
| 6,514,244 B2 | 2/2003 | Pope |
| 6,517,484 B1 | 2/2003 | Wilk et al. |
| 6,524,250 B1 | 2/2003 | Weber |
| 6,540,679 B2 | 4/2003 | Slayton |
| 6,540,685 B1 | 4/2003 | Rhoads et al. |
| 6,540,700 B1 | 4/2003 | Fujimoto et al. |
| 6,554,771 B1 | 4/2003 | Buil et al. |
| 6,569,099 B1 | 5/2003 | Babaev |
| 6,569,108 B1 | 5/2003 | Sarvazyan et al. |
| 6,572,552 B2 | 6/2003 | Fukukita |
| 6,575,956 B1 | 6/2003 | Brisken et al. |
| 6,595,934 B1 | 7/2003 | Hissong |
| 6,599,256 B1 | 7/2003 | Acker |
| 6,607,498 B2 | 8/2003 | Eshel |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng et al. |
| 6,638,226 B2 | 10/2003 | He et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,666,835 B2 | 12/2003 | Martin |
| 6,669,638 B1 | 12/2003 | Miller et al. |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Lauglin |
| 6,719,694 B2 | 4/2004 | Weng et al. |
| 6,726,627 B1 | 4/2004 | Lizzi et al. |
| 6,825,176 B2 | 4/2004 | Mourad |
| 6,733,449 B1 | 5/2004 | Krishnamurthy et al. |
| 6,749,624 B2 | 6/2004 | Knowlton |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,835,940 B2 | 12/2004 | Morikawa et al. |
| 6,846,290 B2 | 1/2005 | Lizzi et al. |
| 6,875,176 B2 | 4/2005 | Mourad et al. |
| 6,882,884 B1 | 4/2005 | Mosk et al. |
| 6,887,239 B2 | 5/2005 | Elstrom et al. |
| 6,889,089 B2 | 5/2005 | Behl |
| 6,896,657 B2 | 5/2005 | Willis |
| 6,902,536 B2 | 6/2005 | Manna et al. |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood et al. |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng et al. |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |

(56) References Cited

U.S. PATENT DOCUMENTS

| | | |
|---|---|---|
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco et al. |
| 7,303,555 B2 | 12/2007 | Makin et al. |
| 7,327,071 B2 | 2/2008 | Nishiyama et al. |
| 7,331,951 B2 | 2/2008 | Eshel et al. |
| 7,332,985 B2 | 2/2008 | Larson, III et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,510,536 B2 | 3/2009 | Foley et al. |
| 7,530,356 B2 | 5/2009 | Slayton |
| 7,530,958 B2 | 5/2009 | Slayton |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,686,763 B2 | 3/2010 | Vaezy et al. |
| 7,695,437 B2 | 4/2010 | Quistgaard et al. |
| 7,758,524 B2 | 7/2010 | Barthe |
| 7,789,841 B2 | 9/2010 | Huckle et al. |
| 7,824,348 B2 | 11/2010 | Barthe et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,914,453 B2 | 3/2011 | Slayton et al. |
| 7,914,469 B2 | 3/2011 | Torbati |
| 7,931,611 B2 | 4/2011 | Novak et al. |
| 7,955,281 B2 | 6/2011 | Pedersen et al. |
| 7,967,764 B2 | 6/2011 | Lidgren et al. |
| 7,967,839 B2 | 6/2011 | Flock et al. |
| 8,057,389 B2 | 11/2011 | Barthe et al. |
| 8,057,465 B2 | 11/2011 | Sliwa, Jr. et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,166,332 B2 | 4/2012 | Barthe et al. |
| 8,197,409 B2 | 6/2012 | Foley et al. |
| 8,206,299 B2 | 6/2012 | Foley et al. |
| 8,211,017 B2 | 7/2012 | Foley et al. |
| 8,262,591 B2 | 9/2012 | Pedersen et al. |
| 8,273,037 B2 | 9/2012 | Kreindel et al. |
| 8,282,554 B2 | 10/2012 | Makin et al. |
| 8,333,700 B1 | 12/2012 | Barthe et al. |
| 8,366,622 B2 | 2/2013 | Slayton et al. |
| 8,409,097 B2 | 4/2013 | Slayton et al. |
| 8,444,562 B2 | 5/2013 | Barthe et al. |
| 8,480,585 B2 | 7/2013 | Slayton et al. |
| 8,506,486 B2 | 8/2013 | Slayton et al. |
| 8,523,775 B2 | 9/2013 | Barthe et al. |
| 8,535,228 B2 | 9/2013 | Slayton et al. |
| 8,585,618 B2 | 11/2013 | Hunziker et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 * | 5/2014 | Slayton et al. ............... 600/439 |
| 8,726,781 B2 | 5/2014 | Eckhoff et al. |
| 2001/0009997 A1 | 7/2001 | Pope |
| 2001/0009999 A1 | 7/2001 | Kaufman et al. |
| 2001/0014780 A1 | 8/2001 | Martin et al. |
| 2001/0014819 A1 | 8/2001 | Ingle et al. |
| 2001/0031922 A1 | 10/2001 | Weng et al. |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0052550 A1 | 5/2002 | Madsen et al. |
| 2002/0055702 A1 | 5/2002 | Atala |
| 2002/0062077 A1 | 5/2002 | Emmenegger et al. |
| 2002/0062142 A1 | 5/2002 | Knowlton |
| 2002/0072691 A1 | 6/2002 | Thompson et al. |
| 2002/0082528 A1 | 6/2002 | Friedman et al. |
| 2002/0082529 A1 | 6/2002 | Suorsa et al. |
| 2002/0082589 A1 | 6/2002 | Friedman et al. |
| 2002/0087080 A1 | 7/2002 | Slayton et al. |
| 2002/0095143 A1 | 7/2002 | Key |
| 2002/0099094 A1 | 7/2002 | Anderson |
| 2002/0115917 A1 | 8/2002 | Honda et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | Mchale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0055417 A1 | 3/2003 | Truckai et al. |
| 2003/0060736 A1 | 3/2003 | Martin et al. |
| 2003/0065313 A1 | 4/2003 | Koop |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefevbre |
| 2003/0125629 A1 | 7/2003 | Ustuner |
| 2003/0139790 A1 | 7/2003 | Ingle et al. |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002705 A1 | 1/2004 | Knowlton |
| 2004/0010222 A1 | 1/2004 | Nunomura et al. |
| 2004/0015106 A1 | 1/2004 | Coleman |
| 2004/0030227 A1 | 2/2004 | Littrup |
| 2004/0039312 A1 | 2/2004 | Hillstead |
| 2004/0039418 A1 | 2/2004 | Elstrom et al. |
| 2004/0041563 A1 | 3/2004 | Lewin et al. |
| 2004/0041880 A1 | 3/2004 | Ikeda et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Simske |
| 2004/0059266 A1 | 3/2004 | Fry |
| 2004/0068186 A1 | 4/2004 | Ishida et al. |
| 2004/0073079 A1 | 4/2004 | Altshuler et al. |
| 2004/0073113 A1 | 4/2004 | Salgo |
| 2004/0073115 A1 | 4/2004 | Horzewski et al. |

(56) References Cited

U.S. PATENT DOCUMENTS

| | | |
|---|---|---|
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger et al. |
| 2004/0082859 A1 | 4/2004 | Schaer |
| 2004/0102697 A1 | 5/2004 | Evron |
| 2004/0105559 A1 | 6/2004 | Aylward et al. |
| 2004/0122323 A1 | 6/2004 | Vortman et al. |
| 2004/0122493 A1 | 6/2004 | Ishbashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste et al. |
| 2004/0267252 A1 | 12/2004 | Washington et al. |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055073 A1 | 3/2005 | Weber |
| 2005/0061834 A1 | 3/2005 | Garcia et al. |
| 2005/0070961 A1 | 3/2005 | Maki et al. |
| 2005/0074407 A1 | 4/2005 | Smith |
| 2005/0080469 A1 | 4/2005 | Larson |
| 2005/0091770 A1 | 5/2005 | Mourad et al. |
| 2005/0096542 A1 | 5/2005 | Weng et al. |
| 2005/0104690 A1 | 5/2005 | Larson, III et al. |
| 2005/0113689 A1 | 5/2005 | Gritzky |
| 2005/0134314 A1 | 6/2005 | Prather et al. |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard et al. |
| 2005/0197681 A1 | 9/2005 | Barolet et al. |
| 2005/0228281 A1 | 10/2005 | Nefos |
| 2005/0240170 A1 | 10/2005 | Zhang et al. |
| 2005/0251120 A1 | 11/2005 | Anderson et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya et al. |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0229514 A1 | 10/2006 | Wiener |
| 2006/0241440 A1 | 10/2006 | Eshel |
| 2006/0241442 A1 | 10/2006 | Barthe |
| 2006/0241470 A1 | 10/2006 | Novak et al. |
| 2006/0250046 A1 | 11/2006 | Koizumi et al. |
| 2006/0261584 A1 | 11/2006 | Eshel |
| 2006/0282691 A1 | 12/2006 | Barthe |
| 2006/0291710 A1 | 12/2006 | Wang et al. |
| 2007/0032784 A1 | 2/2007 | Gliklich et al. |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1 | 9/2007 | Yaroslavsky et al. |
| 2007/0219605 A1 | 9/2007 | Yaroslavsky et al. |
| 2007/0238994 A1 | 10/2007 | Stecco et al. |
| 2007/0239075 A1 | 10/2007 | Rosenberg et al. |
| 2007/0239079 A1 | 10/2007 | Manstein et al. |
| 2007/0239142 A1 | 10/2007 | Altshuler et al. |
| 2008/0027328 A1 | 1/2008 | Klopotek et al. |
| 2008/0039724 A1 | 2/2008 | Seip et al. |
| 2008/0071255 A1 | 3/2008 | Barthe |
| 2008/0086054 A1 | 4/2008 | Slayton |
| 2008/0097253 A1 | 4/2008 | Pedersen |
| 2008/0139974 A1 | 6/2008 | Da Silva |
| 2008/0146970 A1 | 6/2008 | Litman et al. |
| 2008/0167556 A1 | 7/2008 | Thompson et al. |
| 2008/0183077 A1 | 7/2008 | Moreau-Gobard et al. |
| 2008/0188745 A1 | 8/2008 | Chen et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0221491 A1 | 9/2008 | Slayton |
| 2008/0223379 A1 | 9/2008 | Stuker et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294073 A1 | 11/2008 | Barthe et al. |
| 2008/0319356 A1 | 12/2008 | Cain et al. |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0253988 A1 | 10/2009 | Slayton et al. |
| 2009/0299175 A1 | 12/2009 | Bernstein et al. |
| 2009/0318909 A1 | 12/2009 | Debenedictis et al. |
| 2010/0011236 A1 | 1/2010 | Barthe et al. |
| 2010/0022919 A1 | 1/2010 | Peterson |
| 2010/0022922 A1 | 1/2010 | Barthe et al. |
| 2010/0042020 A1 | 2/2010 | Ben-Ezra |
| 2010/0049178 A1 | 2/2010 | Deem et al. |

(56) References Cited

U.S. PATENT DOCUMENTS

| | | |
|---|---|---|
| 2010/0063422 A1 | 3/2010 | Hynynen et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe et al. |
| 2010/0280420 A1 | 11/2010 | Barthe et al. |
| 2010/0286518 A1 | 11/2010 | Lee et al. |
| 2011/0040171 A1 | 2/2011 | Foley et al. |
| 2011/0040190 A1 | 2/2011 | Jahnke et al. |
| 2011/0087099 A1 | 4/2011 | Eshel et al. |
| 2011/0087255 A1 | 4/2011 | Mccormack et al. |
| 2011/0112405 A1 | 5/2011 | Barthe et al. |
| 2011/0178444 A1 | 7/2011 | Slayton et al. |
| 2011/0190745 A1 | 8/2011 | Uebelhoer et al. |
| 2011/0264012 A1 | 10/2011 | Lautzenhiser et al. |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0111339 A1 | 5/2012 | Barthe et al. |
| 2012/0143056 A1 | 6/2012 | Slayton et al. |
| 2012/0165668 A1 | 6/2012 | Slayton et al. |
| 2012/0165848 A1 | 6/2012 | Slayton et al. |
| 2012/0197120 A1 | 8/2012 | Makin et al. |
| 2012/0197121 A1 | 8/2012 | Slayton et al. |
| 2012/0215105 A1 | 8/2012 | Slayton et al. |
| 2012/0271294 A1 | 10/2012 | Barthe et al. |
| 2012/0296240 A1 | 11/2012 | Azhari et al. |
| 2012/0316426 A1 | 12/2012 | Foley et al. |
| 2012/0330197 A1 | 12/2012 | Makin et al. |
| 2012/0330222 A1 | 12/2012 | Barthe et al. |
| 2012/0330223 A1 | 12/2012 | Makin et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018286 A1 | 1/2013 | Slayton et al. |
| 2013/0046209 A1 | 2/2013 | Slayton et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0096471 A1 | 4/2013 | Slayton et al. |
| 2013/0190659 A1 | 7/2013 | Slayton et al. |
| 2013/0211258 A1 | 8/2013 | Barthe et al. |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0303904 A1 | 11/2013 | Barthe et al. |
| 2013/0303905 A1 | 11/2013 | Barthe et al. |
| 2013/0310863 A1 | 11/2013 | Barthe et al. |
| 2014/0082907 A1 | 3/2014 | Barthe |
| 2014/0142430 A1 | 5/2014 | Slayton et al. |
| 2014/0148834 A1 | 5/2014 | Barthe et al. |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |

FOREIGN PATENT DOCUMENTS

| | | | |
|---|---|---|---|
| DE | 10219217 | | 11/2003 |
| DE | 10219297 | | 11/2003 |
| DE | 20314479 | | 3/2004 |
| EP | 0344773 | | 12/1989 |
| EP | 1479412 | | 11/1991 |
| EP | 0473553 | A | 3/1992 |
| EP | 0661029 | A | 7/1995 |
| EP | 1050322 | | 11/2000 |
| EP | 1234566 | | 8/2002 |
| EP | 1262160 | | 12/2002 |
| EP | 1374944 | A | 1/2004 |
| GB | 2113099 | | 8/1983 |
| JP | 63036171 | | 2/1988 |
| JP | 03048299 | | 3/1991 |
| JP | 3123559 | | 5/1991 |
| JP | 03136642 | | 6/1991 |
| JP | 4089058 | | 3/1992 |
| JP | 04150847 | | 5/1992 |
| JP | 7080087 | | 3/1995 |
| JP | 07505793 | | 6/1995 |
| JP | 7222782 | | 8/1995 |
| JP | 09047458 | | 2/1997 |
| JP | 11505440 | | 5/1999 |
| JP | 11506636 | | 6/1999 |
| JP | 2000166940 | | 6/2000 |
| JP | 2001170068 | | 6/2001 |
| JP | 2002078764 | | 3/2002 |
| JP | 2002515786 | | 5/2002 |
| JP | 2002521118 | | 7/2002 |
| JP | 2002537939 | | 11/2002 |
| JP | 2003050298 | | 2/2003 |
| JP | 2003204982 | | 7/2003 |
| JP | 2004147719 | | 5/2004 |
| JP | 2005503388 | | 2/2005 |
| JP | 2005527336 | | 9/2005 |
| JP | 2005323213 | | 11/2005 |
| JP | 2006520247 | | 9/2006 |
| JP | 2007505793 | A | 3/2007 |
| JP | 2009518126 | | 5/2009 |
| JP | 2010517695 | | 5/2010 |
| KR | 1020010024871 | | 3/2001 |
| KR | 100400870 | B1 | 10/2003 |
| KR | 1020060113930 | | 11/2006 |
| KR | 1020070065332 | | 6/2007 |
| KR | 1020070070161 | | 7/2007 |
| KR | 1020070098856 | | 10/2007 |
| KR | 1020070104878 | | 10/2007 |
| KR | 1020070114105 | | 11/2007 |
| WO | 9625888 | | 8/1996 |
| WO | 9639079 | A1 | 12/1996 |
| WO | 9735518 | | 10/1997 |
| WO | 9832379 | | 7/1998 |
| WO | 9933520 | | 7/1999 |
| WO | 9949788 | | 10/1999 |
| WO | 0006032 | | 2/2000 |
| WO | 0015300 | | 3/2000 |
| WO | 0021612 | | 4/2000 |
| WO | 0053113 | | 9/2000 |
| WO | 0128623 | | 4/2001 |
| WO | 0182777 | | 11/2001 |
| WO | 0182778 | | 11/2001 |
| WO | 0187161 | | 11/2001 |
| WO | 0209813 | | 2/2002 |
| WO | 0224050 | | 3/2002 |
| WO | 02092168 | A | 11/2002 |
| WO | 020292168 | | 11/2002 |
| WO | 03053266 | A | 7/2003 |
| WO | 03065347 | | 8/2003 |
| WO | 03070105 | | 8/2003 |
| WO | 03077833 | | 8/2003 |
| WO | 03086215 | | 10/2003 |
| WO | 03096883 | | 11/2003 |
| WO | 03099177 | | 12/2003 |
| WO | 03101530 | | 12/2003 |
| WO | 2004000116 | A | 12/2003 |
| WO | 2004080147 | | 9/2004 |
| WO | 2004110558 | | 12/2004 |
| WO | 2005011804 | A | 2/2005 |
| WO | 2005065408 | | 7/2005 |
| WO | 2005090978 | | 9/2005 |
| WO | 2006036870 | | 4/2006 |
| WO | 2006042163 | A | 4/2006 |
| WO | 2006042168 | | 4/2006 |
| WO | 2006042201 | | 4/2006 |
| WO | 2006065671 | | 6/2006 |
| WO | 2006082573 | | 8/2006 |
| WO | 2007067563 | A | 6/2007 |

(56) References Cited

FOREIGN PATENT DOCUMENTS

| WO | 2008024923 A2 | 2/2008 |
|---|---|---|
| WO | 2008036622 A | 3/2008 |
| WO | 2009013729 | 1/2009 |
| WO | 2009149390 A1 | 12/2009 |
| WO | 2014055708 A1 | 4/2014 |

OTHER PUBLICATIONS

Seip, Ralf, et al., "Noninvasive Detection of Thermal Effects Due to Highly Focused Ultrasonic Fiels," IEEE Symposium, pp. 1229-1232, vol. 2, Oct. 3-Nov. 1993.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Simon et al., "Applications of Lipid-Coated Microbubble Ultrasonic Contrast to Tumor Therapy," Ultrasound in Med & Biol. vol. 19, No. 2, pp. 123-125 (1993).

Smith, Nadine Barrie, et al., "Non-Invasive In Vivo Temperature Mapping of Ultrasound Heating Using Magnetic Resonance Techniques", 1994 Ultrasonics Symposium, pp. 1829-1832, vol. 3.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

Ueno, S., et al., "Ultrasound Thermometry in Hyperthermia", 1990 Ultrasonic Symposium, pp. 1645-1652.

Wang, H., et al., "Limits on Focused Ultrasound for Deep Hyperthermia", 1994 Ultrasonic Symposium, Nov. 1-4, 1994, pp. 1869-1872, vol. 3.

Wasson, Scott, "NVIDIA's GeFroce 7800 GTX graphics processor Power MADD," http://techreport.com/reviews/2005q2/geforce-7800gtx/index.x?pg=1, Jun. 22, 2005, 4 pages.

White et al "Selective Creation of Thermal Injury Zones in the Superficial Musculoaponeurotic System Using Intense Ultrasound Therapy," Arch Facial Plastic Surgery, Jan./Feb. 2007, vol. 9, No. 1.

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Arthur et al., "Non-invasive estimation of hyperthermia temperatures with ultrasound," Int. J. Hyperthermia, Sep. 2005, 21(6), pp. 589-600.

Barthe et al., "Ultrasound therapy system and abiation results utilizing miniature imaging/therapy arrays," Ultrasonics Symposium, 2004 IEEE, Aug. 23, 2004, pp. 1792-1795, vol. 3.

Calderhead et al, One Mechanism Behind LED Photo-Therapy for Wound Healing and Skin Rejuvenation: Key Role of the Mast Cell, Laser Therapy, Jul. 2008, pp. 141-148, 17.3.

Chen, L. et al., "Effect of Blood Perfusion on the ablation of liver perenchyma with high intensity focused ultrasound," Phys. Med. Biol; 38:1661-1673; 1993b.

Coon, Joshua et al., "Protein identification using sequential ion/ion reactions and tandem mass spectometry" Proceedings of the National Academy of Sciences of the USA, vol. 102, No. 27, Jul. 5, 2005, pp. 9463-9468.

European Examination Report in related Application No. 05808908.7 dated Jun. 29, 2009.

European Examination Report in related Application No. 05810308.6 dated Jun. 29, 2009.

European Examination Report in related Application No. 09835856.7 dated Apr. 11, 2004.

European Examination Report in related Application No. 10185100.4 dated Jan. 6, 2014.

European Examination Report in related Application No. 10185120.2 dated Jan. 22, 2014.

Corry, Peter M., et al., "Human Cancer Treatment with Ultrasound", IEEE Transactions on Sonics and Ultrasonics, vol. SU-31, No. 5, Sep. 1984, pp. 444,456.

Damianou et al., Application of the Thermal Dose Concept for Predicting the Necrosed Tissue Volume During Ultrasound Surgery, 1993 IEEE Ultrasound Symposium, pp. 1199-1202.

Daum et al., "Design and Evaluation of a Feedback Based Phased Array System for Ultrasound Surgery," IEEE Transactions on Ultrasonics, Feroelectronics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Decision of the Korean Intellectual Property Tribunal dated Jun. 28, 2013 regarding Korean Patent No. 10-1142108, which is related to the pending application and/or an application identified in the Table on the pp. 2-5 of the information Disclosure Statement herein (English translation, English translation certification, and Korean decision included).

Fry, W.J. et al., "Production of Focal Destructive Lesions in the Central Nervous System with Ultrasound," J. Neurosurg., 11:471-478; 1954.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9.

Harr, G.R. et al., "Tissue Destruction with Focused Ultrasound in Vivo," Eur. Urol. 23 (suppl. 1):8-11; 1993.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of accoustically activated uptake of drugs from Pluronic micelles," BMD Cancer 2002, 2:20k, Aug. 30, 2002, pp. 1-6.

International Search Report and Written Opinion dated Jan. 23, 2014 in Application No. PCT/US2012/046122.

International Search Report and Written Opinion dated Jan. 23, 2014 in Application No. PCT/US2012/046123.

International Search Report and Written Opinion dated Jan. 28, 2012 in Application No. PCT/US2012/046327.

International Search Report and Written Opinion dated Jan. 28, 2013 in Application No. PCT/US2012/046125.

International Search Report and Written Opinion dated Feb. 14, 2013 in Application No. PCT/US2011/001361.

International Search Report and Written Opinion dated Feb. 14, 2013 in Application No. PCT/US2011/001362.

International Search Report and Written Opinion dated Feb. 14, 2013 in Application No. PCT/US2011/001366.

International Search Report and Written Opinion dated Apr. 6, 2012 in Application No. PCT/US2011/001366.

International Search Report and Written Opinion dated Apr. 6, 2012 in Application No. PCT/US2011/001367.

Jeffers et al., "Evaluation of the Effect of Cavitation Activity on Drug-Ultrasound Synergisms," 1993 IEEE Ultrasonics Symposium, pp. 925-928.

Jenne, J., et al., "Temperature Mapping for High Energy US-Therapy", 1994 Ultrasonics Symposium, pp. 1879-1882.

(56) References Cited

OTHER PUBLICATIONS

Johnson, S.A., et al., "Non-Intrusive Measurement of Microwave and Ultrasound-Induced Hyperthermia by Acoustic temperature Tomography", Ultrasonics Symposium Proceedings, pp. 977-982.

Madersbacher, S. et al., "Tissue Ablation in Bening Prostatic Hyperplasia with High Intensity Focused Ultrasound," Dur. Urol., 23 (suppl. 1):39-43; 1993.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Miniaturized Ultrasound Arrays for Interstitial Ablation and Imaging," UltraSound Med. Biol. 2005, Nov. 1, 2005, pp. 1539-1550, vol. 31(11).

Makin et al., "Confirmal Bulk Ablation and Therapy Monitoring Using Intracorporeal Image-Treat Ultrasound Arrays", 4th International Symposium on Therapeutic Ultrasound, Sep. 19, 2004.

Manohar et al, "Photoacoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling nad Experiments," J. Acoust. Soc. Am., Oct. 1, 2005, pp. 2715-2724, vol. 118(4).

Mitragotri, Samir; "Healing sound: the use of ultrasound in drug delivery and other therapeutic applications," Nature Reviews; Drug Delivery, pp. 255-260, vol. 4.

Paradossi et al., "Poly(vinyl alcohol) as versatile biomaterial for potential biomedical applications," Journal of Materials Science: Materials in Medicine, 2003, pp. 687-691, vol. 14.

PCT/US2012/046122 International Search Report Jan. 30, 2013.
PCT/US2012/046123 International Search Report Jan. 28, 2013.
PCT/US2012/046125 International Search Report Jan. 28, 2013.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Saad et al., "Ultrasound-Enhanced Effects of Adriamycin Against Murine Tumors," Ultrasound in Med. & Biol. vol. 18, No. 8, pp. 715-723 (1992).

Sanghvi, N.T., et al., "Transrectal Ablation of Prostate Tissue Using Focused Ultrasound," 1993 Ultrasonics Symposium, IEEE, pp. 1207-1210.

PCT International Search Report and Written Opinion, PCT/US2014/030779, Sep. 1, 2014, 8 pages.

European Patent Office, Examination Report, EP 07814933.3, Aug. 5, 2014, 5 pages.

European Patent Office, Examination Report, EP 05798870.1, Oct. 20, 2014, 5 pages.

European Patent Office, Examination Report, EP 10185100.4, Oct. 24, 2014, 4 pages.

European Patent Office, Examination Report, EP 10185112.9, Oct. 24, 2014, 5 pages.

European Patent Office, Examination Report, EP 10185117.8, Oct. 24, 2014, 5 pages.

European Patent Office, Examination Report, EP 10185120.2, Oct. 24, 2014, 4 pages.

\* cited by examiner

METHODS AND SYSTEMS FOR GENERATING THERMAL BUBBLES FOR IMPROVED ULTRASOUND IMAGING AND THERAPY

CROSS-REFERENCE TO RELATED APPLICATIONS

This application is a continuation of U.S. patent application Ser. No. 12/954,484 entitled "METHODS AND SYSTEMS FOR GENERATING THERMAL BUBBLES FOR IMPROVED ULTRASOUND IMAGING AND THERAPY" filed on Nov. 24, 2010, issued as U.S. Pat. No. 8,715,186 on May 6, 2014, which claims the benefit of priority from U.S. Provisional No. 61/293,916 filed Nov. 24, 2009, all of which are incorporated in its entirety by reference, herein.

FIELD OF INVENTION

Embodiments of the present invention generally relate to therapeutic treatment systems, and more particularly, to methods and systems for generating thermal bubbles for improved ultrasound imaging and therapy.

BACKGROUND

Ultrasound has long been used for diagnostic imaging applications. More recently however, several new therapeutic applications for ultrasound are being discovered.

SUMMARY

Various embodiments of the present invention provide a method and system uniquely capable of generating thermal bubbles for improved ultrasound imaging and therapy.

In various embodiments, the physical mechanisms for generating thermal bubbles can comprise one or more of the following: (1) selective absorption of ultrasound energy within a bubbly medium due to enhanced attenuation from scattering; (2) enhanced thermal gradient in a micro-bubble rich region due to enhanced viscous losses from stable cavitation; (3) enhanced thermal response due to ultrasound-gas-vapor voids; and (4) enhanced deposition of thermal energy from inertial cavitation events.

In various embodiments, providing ultrasound energy to cell membranes or tissues with thermal bubbles ultrasound imaging and therapy. For example, in various embodiments, the permeability and/or transparency of cell membranes can be modulated. For example, in some embodiments, the permeability and/or transparency of cell membranes is increased. In some embodiments, heating can cause better diffusion of a material or a drug through the layers of skin tissue. Cavitation and radiation force involves sustained oscillatory motion of bubbles (a.k.a. stable cavitation) and/or rapid growth and collapse of bubbles (a.k.a. inertial cavitation). Resulting fluid velocities, shear forces and shock waves can disrupt cell membranes or tissues and induce chemical changes in the surrounding medium. The collapse of bubbles can additionally increase the bubble core temperature and induce chemical changes in the medium (e.g., generate highly reactive species, such as free radicals). Each of the above effects can impact ultrasound imaging and therapy effectiveness. In addition, other ways to impact ultrasound imaging and therapy include melting or mechanically disrupting thermally sensitive or mechanically fragile substances, such as medicant-carrying liposomes and/or other chemical loaded, gas or liquid filled stabilized spheres, analogous to local delivery.

In some embodiments, ultrasound imaging and therapy can be enhanced when shock waves generated upon collapse of bubbles disrupt the stratum corneum and thereby enhance skin permeability. Likewise, ultrasound imaging and therapy effectiveness can be enhanced when shock waves transiently compromise the integrity of cell membranes or tissues, or when local free-radical concentration enhances medicant toxicity. Moreover, certain medicants can be activated and/or released using energy. In that regard, a medicant encapsulated in a carrier can be released at the site of interest using energy (e.g., acoustic energy). For example, U.S. Pat. No. 6,623,430, entitled "Method and Apparatus for Safely Delivering Medicants to a Region of Tissue Using Imaging, Therapy and Temperature Monitoring Ultrasonic System", which is hereby incorporated by reference in its entirety.

In various embodiments, a region of interest (or "ROI") is located within one of the nonviable epidermis (i.e., the stratum corneum), the viable epidermis, the dermis, the subcutaneous connective tissue and fat, and the muscle. Depths may be in the range of about 0 mm to about 3 mm, 5 mm, 8 mm, 10 mm, 25 mm, 60 mm, 80 mm, or 100 mm or more. In accordance with various embodiments, the ROT is located about 20 mm to about 30 mm below the stratum corneum. Further, a plurality of ROI can be treated, and in some embodiments, simultaneously. For example, the ROI may consist of one or more organs or a combination of tissues either superficial or deep within the body.

In various embodiments, the method and system is uniquely capable of disrupting cell membranes or tissues and inducing chemical changes in the surrounding medium at either a single or multiple layers of skin tissue simultaneously (e.g., a plurality of depths within a cell membrane or tissue simultaneously). For example, in one embodiment, one frequency of acoustic energy at one skin layer might generate shock waves upon collapse of bubbles to disrupt the stratum corneum and thereby enhance skin permeability. A different frequency of acoustic energy at a different skin layer might simply provide heat to cause better diffusion of medicants through the layers of skin tissue. Yet another frequency of acoustic energy at a different skin layer might compromise the integrity of cell membranes or tissues, or generate local free-radicals to enhance or reduce medicant toxicity. In various embodiments, acoustic energy can be deposited in three-dimensions and at variable depths to selectively increase tissue permeability to thereby steer or guide the medicant through the tissue to a region of interest.

In various embodiments, the methods and systems disclosed herein contemplate the use of unfocused, focused, or defocused acoustic energy at variable spatial and/or temporal energy settings, in the range of about 1 kHz-100 MHz (e.g. about 1 kHz-50 kHz, 50 kHz-100 kHz, 100 kHz-500 kHz, 500 kHz-1 MHz, 3 MHz-7 MHz, 1 MHz-20 MHz, 1 MHz-10 MHz, 10 MHz-50 MHz, and/or 50 MHz-100 MHz, and any ranges or combinations of ranges), and at variable tissue depths. In various embodiments, the tissue depth can include, but are not limited to, 0-1 mm, 1 mm-2 mm, 2 mm-3 mm, 3 mm-4 mm, 4 mm-5 mm, 5 mm-6 mm, 6 mm-7 mm, 7 mm-8 mm, and 8 mm or more, and any ranges or combinations of ranges. The unique ability to customize acoustic energy output and target a particular region of interest makes possible highly accurate and precise thermal bubble formation.

In various embodiments, a system comprises a probe, a control system, and a display or indicator system. The probe can comprise various probe and/or transducer configurations, In various embodiments, the probe delivers unfocused, focused, or defocused ultrasound energy to the region of interest. Imaging and/or monitoring may alternatively be coupled and/or co-housed with a system contemplated by embodiments of the present invention.

In various embodiments, the control system and display system can also optionally comprise various configurations for controlling probe and system functionality, including for example, a microprocessor with software and a plurality of input/output devices, a system for controlling electronic and/or mechanical scanning and/or multiplexing of transducers, a system for power delivery, systems fir monitoring, systems for sensing the spatial position of the probe and/or transducers, and systems for handling user input and recording treatment results, among others.

In various embodiments, a system for generating thermal bubbles for improved ultrasound imaging and therapy includes a control system configured for control of the system, a probe configured for generating thermal bubbles, and a display system.

In various embodiments, a system for imaging thermal bubbles includes a control system configured for control of the system, a probe configured for imaging thermal bubbles, and a display system.

In various embodiments, a method for generating thermal bubbles for improved ultrasound imaging and therapy includes the steps of providing a source of acoustic energy, coupling the acoustic energy to a region of interest, and focusing the acoustic energy to the region of interest to generate thermal bubbles, wherein the source frequency of the acoustic energy is in the range of about 10 kHz to about 30 MHz.

In various embodiments, a method for generating thermal bubbles to evoke a cellular response includes the steps of providing a source of acoustic energy, coupling the acoustic energy to a region of interest; and focusing the acoustic energy to the region of interest to generate thermal bubbles, wherein the source frequency of the acoustic energy is in the range of about 10 kHz to about 30 MHz (e.g., about 10 kHz-50 kHz, 50 kHz-100 kHz, 100 kHz-500 kHz, 500 kHz-1 MHz, 1 MHz-10 MHz, and/or 10 MHz-30 MHz or overlapping ranges therein), and evoking a cellular response. In various embodiments the cellular response comprises one or more of a wound healing response, an immune histological response, heat-shock protein expression, programmed cell death, wound debridement, keloid/scar healing, and increased localized micro-circulation.

In various embodiments, a method for generating thermal bubbles to affect a chemical moiety includes the steps of providing a source of acoustic energy, coupling the acoustic energy to a region of interest; and focusing the acoustic energy to the region of interest to generate thermal bubbles, wherein the source frequency of the acoustic energy is in the range of about 10 kHz to about 30 MHz (e.g., about 10 kHz-50 kHz, 50 kHz-100 kHz, 100 kHz-500 kHz, 500 kHz-1 MHz, 1 MHz-10 MHz, and/or 10 MHz-30 MHz, or overlapping ranges therein) and evoking an effect on a chemical moiety. In various embodiments, the effect includes enhancing the delivery or augmenting the activation of the chemical moiety.

In various embodiments, a method for optimization of therapy includes concomitant monitoring of bubble activity by monitoring (a) one or more non-thermal responses, (b) one or more thermal responses and/or (c) one or more tissue property changes.

In several embodiments, the systems (and methods thereof) comprise the use of thermal bubbles in which the source frequency of the acoustic energy is about 1-10 MHz for therapy (e.g., 4 or 7 MHz) and 5-25 MHz for imaging (e.g., 18 MHz).

BRIEF DESCRIPTION OF THE DRAWINGS

The subject matter of various embodiments of the invention is particularly pointed out in the claims. Various embodiments of the invention, both as to organization and method of operation, may be understood by reference to the following description taken in conjunction with the accompanying drawing figures, in which like parts may be referred to by like numerals, and:

DETAILED DESCRIPTION

Several embodiments of the present invention may be described herein in terms of various functional components and processing steps. It should be appreciated that such components and steps may be realized by any number of hardware components configured to perform the specified functions and processes. For example, various embodiments of the present invention may employ various medical treatment devices, visual imaging and display devices, input terminals and the like, which may carry out a variety of functions and processes under the control of one or more control systems or other control devices. In addition, various embodiments of the present invention may be practiced in any number of medical contexts and the embodiments relating to a method and system for generating thermal bubbles for improved ultrasound imaging and therapy, as described herein, are merely indicative of embodiments of applications for the invention. For example, the principles, features and methods discussed may be applied to any medical application. Further, various aspects of embodiments of the present invention may be suitably applied to other applications.

Figure 1:
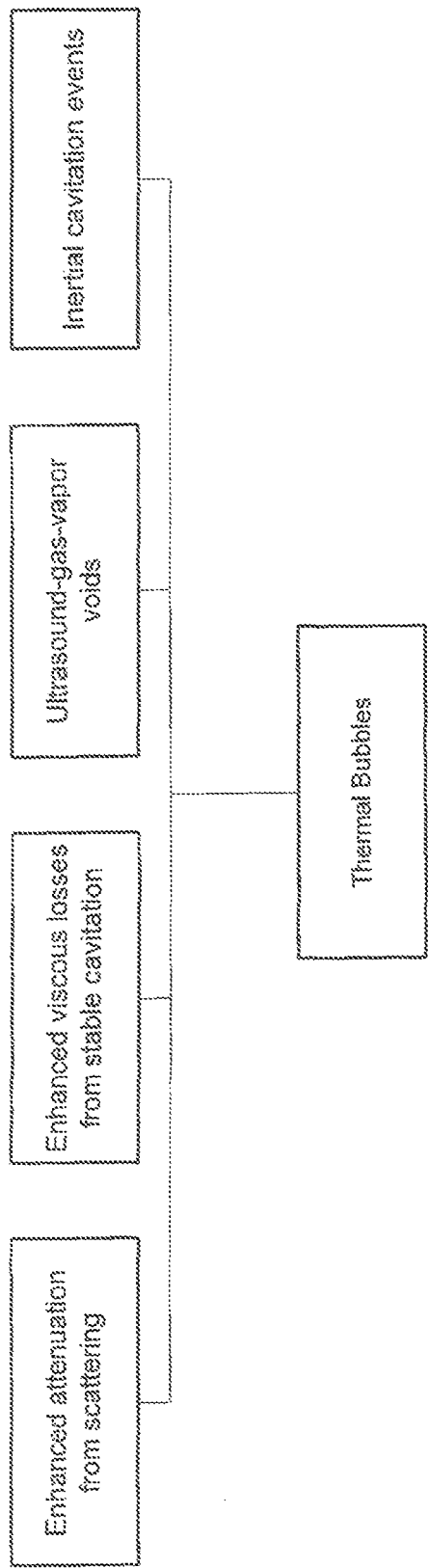
FIG. 1 illustrates a block diagram of a method for generating thermal bubbles for improved ultrasound imaging and therapy in accordance with various embodiments of the present invention.

In various embodiments of systems, and as illustrated in FIG. 1, the physical mechanisms for generating thermal bubbles can comprise: (1) selective absorption of ultrasound energy within a bubbly medium due to enhanced attenuation from scattering; (2) enhanced thermal gradient in a micro-bubble rich region due to enhanced viscous losses from stable cavitation; (3) enhanced thermal response due to ultrasound-gas-vapor voids; and/or (4) enhanced deposition of thermal energy from inertial cavitation events.

Each one of these mechanisms can be modulated either individually or used in combination with a thermal tissue effect. In various embodiments, the source frequency is between 1 kHz-100 MHz, 5 kHz-50 MHz, and/or 10 kHz-30 MHz (e.g., about 1 kHz-50 kHz, 50 kHz-100 kHz, 100 kHz- 500 kHz, 500 kHz-1 MHz, 1 MHz-10 MHz, and/or 10 MHz-30 MHz, or overlapping ranges therein).

In various embodiments, the activation source powers are dependent on the frequency, bubble size distribution, bubble density and tissue. For example, in some embodiments, the lower the frequency, the less intense field is required to initiate thermal bubble activity. In some embodiments, the higher the nominal bubble size, the lower the source frequency at which the gas bodies will resonate. In some embodiments, the higher the local concentration of gas bodies, the greater effect with thermal bubbles can be achieved.

A wide range of transducer design configurations are used in accordance with several embodiments, as further discussed below. These thermal bubble effects can also be leveraged to augmented imaging and treatment monitoring.

The methods and systems according to several embodiments disclosed herein contemplate the use of unfocused, focused, or defocused acoustic energy at variable spatial and/or temporal energy settings, in the range of about 1 kHz-100 MHz (e.g., about 1 kHz-50 kHz, 50 kHz-100 kHz, 100 kHz-500 kHz, 500 kHz-1 MHz, 1 MHz-10 MHz, 10 MHz-30 MHz, and/or 30 MHz-100 MHz, or overlapping ranges therein), and at variable tissue depths. The unique ability to customize acoustic energy output and target a particular region of interest makes possible highly accurate and precise thermal bubble formation.

In several embodiments, the energy is acoustic energy. In other embodiments, the energy is photon based energy (e.g., IPL, LED, laser, white light, etc., or combinations thereof), or other energy forms, such radio frequency electric currents (including monopolar and bipolar radio-frequency current). In an embodiment, the energy is various combinations of acoustic energy, photon based energy, electromagnetic energy and other energy forms or energy absorbers such as cooling.

One or more of a transducer and/or transduction element configuration, a lens, and mechanical movement of a transducer may facilitate targeting of a particular region of interest and/or thermal bubble formation at specific locations.

In accordance with a method according to several embodiments, thermal bubbles act as contrast agents (e.g., markers or boundaries) for ultrasound imaging and therapy. In this manner, a region of interest can be marked or defined such that acoustic energy can be locally applied at for example, a cell, tissue, gland, fiber, or tumor. A boundary can be in any two-dimensional or three-dimensional configuration suitable for defining a region of interest for acoustic energy deposition (e.g., circle, square, triangle, sphere, cube, cone, or any arbitrary shape). The acoustic energy deposited therein may be for any therapeutic purpose now known or later devised (e.g., for ablative or non-ablative purposes).

In accordance with another method, just as thermal bubbles are used as boundaries for acoustic energy inclusion, as described herein, thermal bubbles can be used as boundaries for acoustic energy exclusion. In other words, thermal bubbles can be used to protect or to avoid various cells, tissues, glands, fibers, and/or regions of even higher acoustic impedance or sensitivity, for example. In some embodiments, bubbles are used to partially or fully isolate a region of interest.

Because thermal bubbles exhibit high acoustic impedance, in accordance with some embodiments of a method, they are used to concentrate acoustic energy deposition within a region of interest. For example, thermal bubbles may be created in such a manner so as to "funnel" acoustic energy as it moves from the energy source to the region of interest, thereby concentrating acoustic energy at the deposition site.

An acoustical impedance mismatch can be created between the thermal bubble and the surround tissue. This acoustical mismatch can cause acoustic energy traveling through tissue to reflect, deflect, and/or scatter upon contact with the thermal bubble.

In various embodiments, a method of providing non-invasive ultrasound treatment, can comprise coupling an acoustic source to a surface of skin; providing a first acoustic energy into a region of interest below the surface; creating thermal bubbles in a first portion of the region of interest; providing a second acoustic energy into a second portion of the region of interest; and stimulating a bio-effect in the second portion of the region of interest.

In one embodiment, the method can comprise forming a boundary comprising the thermal bubbles. In one embodiment, the method can comprise reflecting a portion of the second acoustic energy off of at least one of the thermal bubbles. In one embodiment, the method can comprise directing the portion of the second portion of the second acoustic energy away from tissue outside of the region of interest from the second acoustic energy. In one embodiment, the method can comprise protecting the tissue outside of the region of interest from the second acoustic energy. In one embodiment, the tissue outside of the region of interest comprises an internal organ. In one embodiment, the method can comprise directing the portion of the second portion of the second acoustic energy into the second portion of the region of interest.

In one embodiment, the method can comprise scattering at least a portion of the second acoustic energy. In one embodiment, the method can comprise concentrating the second acoustic energy into the second portion of the region of interest. In one embodiment, the method can comprise controlling a size of the thermal bubbles. In one embodiment, the method can comprise increasing a temperature of the first portion of the region of interest. In one embodiment, the method can comprise controlling a size of the thermal bubbles. In one embodiment, the method can comprise surrounding the second portion of the region of interest with the boundary.

In one embodiment, the method can comprise creating a thermal lesion in the second portion of the region of interest. In one embodiment, the method can comprise cosmetically enhancing the skin. In one embodiment, the method can comprise treating the region of interest. In one embodiment, the method the stimulating a bio-effect in the second portion of the region of interest is reducing a volume of tissue. In one embodiment, the method can comprise tightening a portion of the surface of the skin. In one embodiment, the method can comprise providing a third acoustic energy to region of interest. In one embodiment, the method can comprise stimulating a second bio-effect in the region of interest.

In various embodiments, a method of cosmetic enhancement can comprise coupling at least one source to a region of interest; directing a first energy into the region of interest; creating a plurality of thermal bubbles in at least one of the region of interest and a non-target region; directing a second energy into the region of interest; and enhancing at least a portion of the region of interest.

In one embodiment, the at least one source comprises an ultrasound source and a pulsed laser. In one embodiment, the first energy is at least one of photon based energy and ultrasound energy. In one embodiment, the second energy is at least one of photon based energy and ultrasound energy. In one embodiment, the method can further comprise ablating tissue in the region of interest.

In one embodiment, the method can comprise tightening skin on a surface of the region of interest. In one embodiment, the method can comprise introducing a chemical moiety configured to enhance the creating the plurality of thermal bubbles. In one embodiment, the method can comprise imaging at least a portion of the region of interest. In one embodiment, the method can comprise locating the plurality of thermal bubbles. In one embodiment, the method can comprise reflecting the second energy off of at least one of the thermal bubbles.

In various embodiments, a method of treating tissue can comprise providing a first energy into a region of interest; creating at least one thermal bubble in the region of interest; providing a second energy into the region of interest; modulating the second energy; and controlling a size of the at least one thermal bubble.

In one embodiment, the method can comprise increasing the size of the at least one thermal bubble. In one embodiment, the method can comprise oscillating between a first size and a second size of the at least one thermal bubble. In one embodiment, the method can comprise stimulating a bio-effect in the region of interest. In one embodiment, the method can comprise inserting a plurality of bubbles into the region of interest. In one embodiment, the method can comprise increasing a temperature within the region of interest. In one embodiment, the method can comprise stimulating a therapeutic effect within the region of interest. In one embodiment, the method can comprise providing a third energy into the region of interest. In one embodiment, the method can comprise thermally injuring a portion of tissue in the region of interest. In one embodiment, the method can comprise cosmetically enhancing at least a portion of the region of interest.

In accordance with some methods, thermal bubbles are also particularly useful in preferential heating applications. For example, various cells, tissues, glands, fibers, and tumors can be either directly or indirectly therapeutically benefited by increases in temperature. And various therapeutic treatments, such as drug delivery, are facilitated by increases in temperature. Heating applications may be carried out alone or in combination with other thermal bubble applications and/or ultrasound imaging or therapy.

As mentioned above, collapse of cavitation bubbles can generate shock waves capable of disrupting cells and tissues and can induce chemical changes in the surrounding medium (e.g., generate highly reactive species, such as free radicals). Because some embodiments of the present invention enable highly accurate and precise thermal bubble formation, cells, tissues, glands, fibers, tumors, etc, can be selectively disrupted to accomplish various therapeutic applications, and various chemical changes can be induced at specific locations.

As noted above, each one of the abovementioned thermal bubble mechanisms can be modulated either individually or used in combination with a thermal tissue effect. In various embodiments, the combination effect of thermal tissue effects with the use of thermal bubbles effectuates and/or modulates a tissue response. In embodiments, use of bubble effects (inter-intracellular shear with a thermal tissue effect, e.g., thermal gradient), activates a wound healing response, an immune histological response, heat-shock protein expression and/or programmed cell death. In embodiments, tissue responses comprise wound debridement, keloid/scar healing, and increased localized micro-circulation.

In some embodiments, the thermal bubble response is maximized with the concomitant use of micro-bubble based formulations, emulsifiers, saponificants and/or emulsions. Thermal bubble use with other chemical moieties (e.g., analgesics, topical anesthetics, antibiotics, antibacterials, antimicrobials retinoids, etc.) may be useful to (1) enhance their delivery and/or (2) to augment their activation.

In some embodiments, selective tissue effects are achieved with a selective thermal-bubble response within one or more tissues (such as deep dermis, subcutaneous layers, etc). In other embodiments, selective tissue responses are enhanced within one or more glandular structures (such as sebaceous gland, sweat gland, hair follicle, etc.), by initiating a localized resonant cavity effect.

In accordance with some embodiments, optimization of therapy is accomplished using concomitant monitoring of bubble activity, for example, monitoring (a) one or more non-thermal responses (e.g., shear, inertial cavitation), (b) one or more thermal responses (e.g., vaporization) and/or (c) one or more tissue property changes. In accordance with one aspect of an embodiment, monitoring of bubble activity comprises imaging.

In various embodiments, the methods and systems for generating thermal bubbles for improved ultrasound imaging and therapy comprise delivering energy to a region of interest ("ROI") within one or more layers of tissue. As mentioned above, in an embodiment, the energy is acoustic energy. In other embodiments, the energy is photon based energy (e.g., IPL, LED, laser, white light, etc.), or other energy forms, such radio frequency electric currents (including monopolar and bipolar radio-frequency current). In an embodiment, the energy is various combinations of acoustic energy, photon-based energy, electromagnetic energy and other energy forms or energy absorbers such as cooling.

In various embodiments, systems and/or methods are configured to produce one or more bio-effects. The term "bio-effects", as used herein, shall be given its ordinary meaning and shall also mean biological effects and include, but not be limited to, effects on tissue (including in vivo, in vitro, in situ and ex vivo tissue), cells, organs and other body parts. Bio-effects include, but are not limited to, incapacitating, partially incapacitating, severing, rejuvenating, removing, ablating, micro-ablating, shortening, manipulating, or removing tissue either instantly or over time, and/or other effects, and/or combinations thereof. Bio-effects include, but are not limited to, tissue manipulation to e.g., facilitate aesthetic effects. Bio-effects also include, but are not limited to, tissue manipulation to e.g., enhance collagen formation or healing. Various bio-effects are further disclosed in U.S. patent application Ser. No. 11/857,989 filed Sep. 19, 2007, published as US2008/0071255, which is incorporated in its entirety by reference, herein. In various embodiments, treatment of a specific subcutaneous tissue to achieve a desired bio-effect uses ultrasound energy from system that may be directed to a specific depth within ROI to reach the targeted subcutaneous tissue. In one embodiment, a bio-effect is cutting tissue. In one embodiment, for example, if it is desired to cut muscle (by applying ultrasound energy at ablative levels), which is a distance below the surface of the skin, ultrasound energy from ultrasound system may be provided at ROI at a level to reach above, below, or approximately at the distance targeted at an ablative level which may be capable of ablating muscle.

In various embodiments, bio-effects may produce a clinical outcome such as a brow lift which can comprise elevating the patient's eyebrows and reducing wrinkles on the patient's brow or forehead region. In some embodiments, the clinical outcome may be the same or similar to traditional invasive surgery techniques, and may comprise the removal of wrinkles through a brow lift or replacement of treatment muscles and/or other tissue and subcutaneous tissue within the forehead (or other regions on the body) with muscle relaxant drugs.

In various embodiments, wrinkles can be partially or completely removed by applying ultrasound energy at ROI along the patient's forehead at levels causing the desired bio-effects. In various embodiments, bio-effects can comprise ablating, micro-ablating, coagulating, severing, partially incapacitating, shortening, removing, or otherwise manipulating tissue or subcutaneous tissue to achieve the desired effect. In various embodiments, method can be used to ablate, micro-ablate, or coagulate a specific tissue, or can be used as part of removing the subcutaneous tissue. Further, in one embodiment, muscle (such as the corrugator supercilii muscle) can be paralyzed and permanently disabled.

In various embodiments, systems and/or methods are configured to initiate and/or stimulate one or more biological responses. In various embodiments, biological responses can comprise, but are not limited to, diathermy, hemostasis, revascularization, angiogenesis, growth of interconnective tissue, tissue reformation, ablation of existing tissue, protein synthesis and/or enhanced cell permeability. Two or more of these biological responses may be combined to facilitate rejuvenation and/or treatment of superficial tissue. In various embodiments, responses to embodiments of systems or embodiments of methods are initiated and/or stimulated by effects can include any biological response initiated and/or stimulated by energy effects, such as, for example: 1) hemostasis, including that stimulated from concentrated ultrasound, 2) subsequent revascularization/angiogenesis, such as that generated from high frequency applications of approximately 2 MHz to 7 MHz or more, 3) growth of interconnective tissue, 4) reformation and/or ablation of existing tissue such as fat, collagen and others, 5) increased cell permeability that may facilitate the possibility of stimulated gene or medication therapy to tissue, and/or increased permeability of certain tissues to a variety of medications initiated by ultrasound frequencies 10 kHz to 10 MHz, 6) enhanced delivery and/or activation of medicants, 7) stimulation of protein synthesis and/or 8) any other possible tissue response such as coagulative necrosis. Thus, for example, in various embodiments, a low intensity dispersed ultrasound field can be generated to provide for angiogenesis, an increased intensity homogeneous or uniform ultrasound field can be generated to provide for diathermy that increases the rate of healing and rejuvenation, and/or high intensity focused and/or unfocused beams can be generated to provide for temporary ablative and hemostatic effects in a variety of depth and positions of human tissue, whereby a summation or a combined effect of rejuvenation is created by combining ultrasound energy fields.

With reference to FIG. 1, in various embodiments, ROI 12 is located within one of the nonviable epidermis (i.e., the stratum corneum), the viable epidermis, the viable dermis, the subcutaneous connective tissue and fat, and the muscle. Further, while only ROI 12 is illustrated, a plurality of ROIs can be treated, and in some embodiments, treated simultaneously. For example, ROI 12 may consist of or comprise of one or more organs or a combination of tissues or subcutaneous tissues, which are either superficial or located deep within the body.

Figure 2:
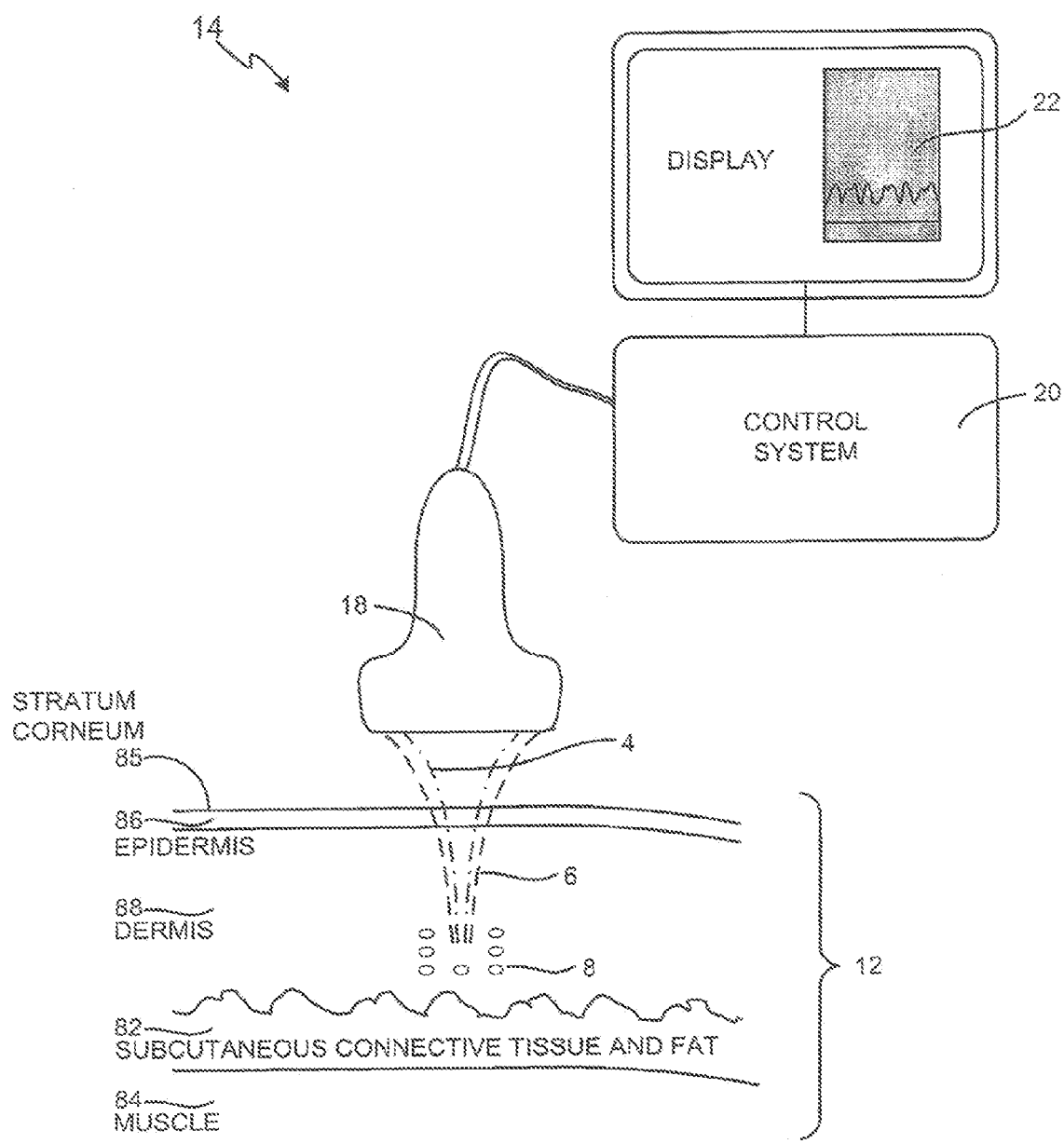
FIG. 2 illustrates a schematic diagram of a treatment system configured to generate thermal bubbles in accordance with an various embodiments of the present invention.

In an embodiment, with reference to FIG. 2, an ultrasound system 14, comprising a control system 20, a probe 18, and a display system 22, is used to deliver first energy 4 and second energy 6 to at least a portion of ROI 12, such as, for example one or more of stratum corneum 85, viable epidermis 86, viable dermis 88, subcutaneous connective tissue and fat 82, and muscle 84. In various embodiments, at least one of first energy 4 and second energy 6 is provided by an acoustic transducer. In one embodiment, first energy 4 and second energy 6 are two different forms of ultrasound energy.

With continued reference to FIG. 2, in various embodiments, a probe 18 is a transducer that delivers first energy 4 and second energy 6 to ROI 12. Either or both of first energy 4 and second energy 6 may be used to produce thermal bubbles 8 or provide ultrasound imaging or therapy. For example, acoustic energy 4 might create a thermal bubble 8 marker or boundary, or "funnel," while acoustic energy 6 provides ultrasound therapy directed to the marker or within the boundary.

In an embodiment, suction is used to attach probe 18 to the patient's body. In this embodiment, a negative pressure differential is created, which enables, probe 18 to attach to stratum corneum 85 by suction. A vacuum-type device can be used to create the suction and the vacuum device can be integral with, detachably connected to, or completely separate from probe 18. Using suction to attach probe 18 to stratum corneum 85 I ensures that probe 18 is properly coupled to stratum corneum 85. Further, using suction to attach probe 18 also reduces the thickness of the tissue to make it easier to reach distinct layers of tissue.

Figure 3:
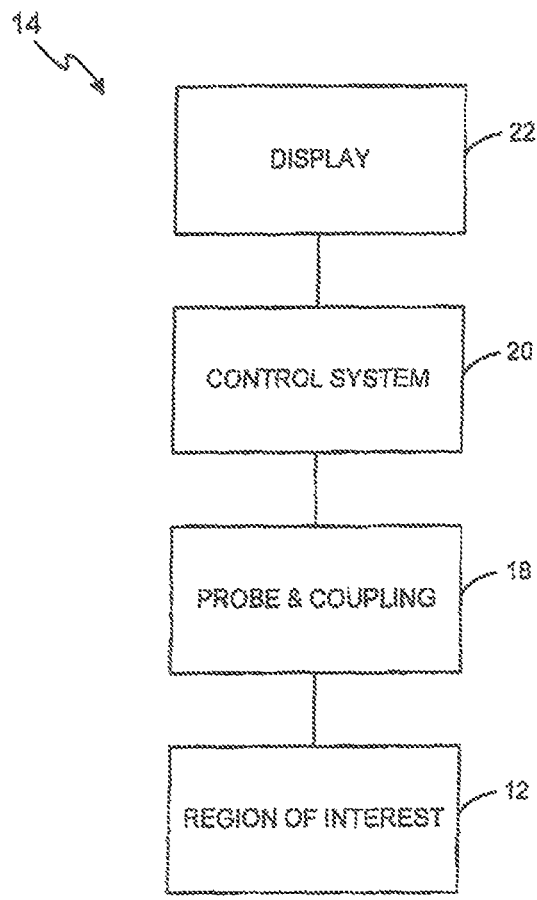
FIG. 3 illustrates a block diagram of a treatment system in accordance with various embodiments of the present invention.

Turning now to the embodiments illustrated in FIG. 3, a system 14 may be capable of emitting ultrasound energy that is focused, unfocused or defocused to treat skin and/or subcutaneous tissue within ROI 12. System 14 may comprise a probe 18, a control system 20, and a display 22. System 14 may be used to delivery energy to, and/or monitor, ROI 12.

With reference to FIGS. 4A-4E, illustrates various embodiments of an acoustic transducer 19 capable of emitting ultrasound energy. This may heat ROI 12 at a specific depth to target a specific tissue or subcutaneous tissue causing that tissue to be ablated, micro-ablated, coagulated, incapacitated, partially incapacitated, rejuvenated, shortened, paralyzed, or removed.

A coupling gel may be used to couple probe 18 to ROI 12 at a surface of stratum corneum 85, for example, a surface of a patient's skin. Ultrasound energy may be emitted in various energy fields in this embodiment. With additional reference to FIG. 4A and FIG. 4B and in this embodiment, the energy fields may be focused, defocused, and/or made substantially planar by transducer 19, to provide many different effects. Energy may be applied in a C-plane or C-scan. For example, in one embodiment, a substantially planar energy field may provide a heating and/or pretreatment effect, a focused energy field may provide a more concentrated source of heat or hypothermal effect, and a non-focused energy field may provide diffused heating effects. It should be noted that the term "non-focused" as used throughout encompasses energy that is unfocused or defocused.

In another embodiment, a transducer 19 may be capable of emitting ultrasound energy for imaging or treatment or combinations thereof. In an embodiment, transducer 19 may be configured to emit ultrasound energy at specific depths in ROI 12 to target a specific tissue. In this embodiment, transducer 19 may be capable of emitting unfocused or defocused ultrasound energy over a wide area in and/or around ROI 12 for treatment purposes.

Figure 4A:
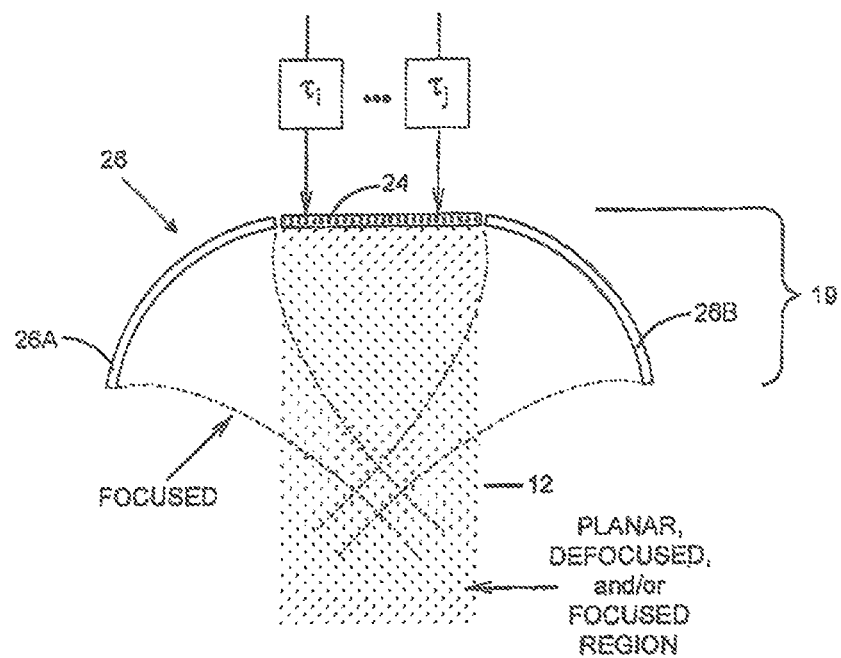
FIGS. 4A, 4B, 4C, 4D, and 4E illustrate cross-sectional diagrams of an transducer used in a system in accordance with various embodiments of the present invention.
Figure 4B:
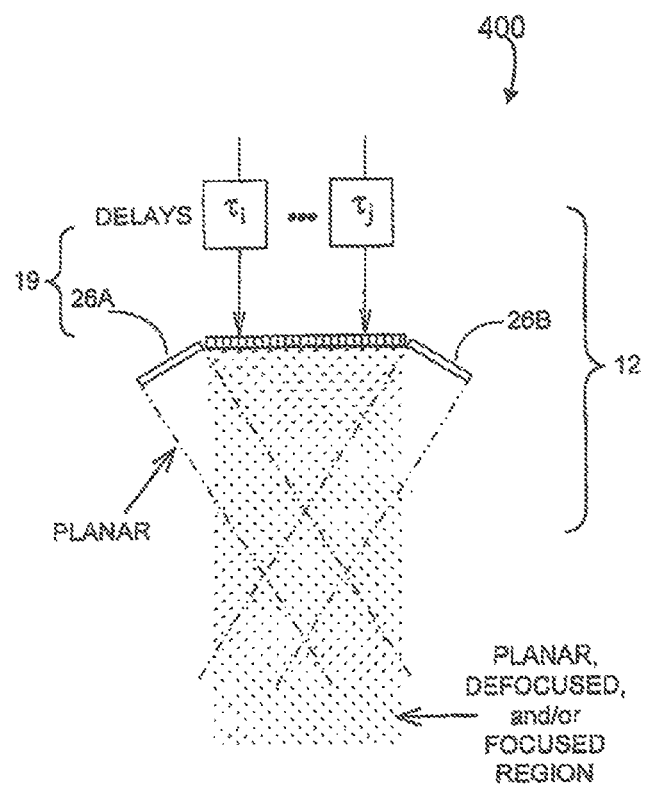

In various embodiments, a transducer 19 may comprise one or more transduction elements 26 for facilitating treatment. Transducer 19 may further comprise one or more transduction elements 26, such as, for example, elements 26A and 26B as illustrated in FIGS. 4A and 4B. One or more transduction elements 26 may comprise piezoelectrically active material, such as lead zirconate titanate (PZT), or other piezoelectrically active material such as, but not limited to, a piezoelectric ceramic, crystal, plastic, and/or composite materials, as well as lithium niobate, lead titanate, barium titanate, and/or lead metaniobate. In addition to, or instead of, a piezoelectrically active material, one or more transduction elements 26 may comprise any other materials configured for generating radiation and/or acoustical energy. Transducer 19 may also comprise one or more matching and/or backing layers coupled to the piezoelectrically active material of the one or more transduction elements 26. Transducer 19 may also be configured with single or multiple damping elements along the one or more transduction element 26.

In an embodiment, the thickness of the transduction element 26 of transducer 19 may be configured to be uniform. That is, the transduction element 26 may be configured to have a thickness that is generally substantially the same throughout.

In another embodiment, the transduction element 26 may also be configured with a variable thickness, and/or as a multiple damped device. For example, the transduction element 26 of transducer 19 may be configured to have a first thickness selected to provide a center operating frequency of a lower range, for example from approximately 1 kHz to 3 MHz. The transduction element 26 may also be configured with a second thickness selected to provide a center operating frequency of a higher range, for example from approximately 3 to 100 MHz or more.

In yet another embodiment, transducer 19 may be configured as a single broadband transducer excited with two or more frequencies to provide an adequate output for raising the temperature within ROI 12 to the desired level. Transducer 19 may also be configured as two or more individual transducers, wherein each transducer 19 may comprise a transduction element 26. The thickness of the transduction elements 26 may be configured to provide center-operating frequencies in a desired treatment range. For example, in an embodiment, transducer 19 may comprise a first transducer 19 configured with a first transduction element 26A having a thickness corresponding to a center frequency range of approximately 1 MHz to 3 MHz, and a second transducer 19 configured with a second transduction element 26B having a thickness corresponding to a center frequency of approximately 3 MHz to 100 MHz or more. Various other ranges of thickness for a first and/or second transduction element 26 can also be realized.

Moreover, in an embodiment, any variety of mechanical lenses or variable focus lenses, e.g. liquid-filled lenses, may also be used to focus and or defocus the energy field. For example, with reference to the embodiments depicted in FIGS. 4A and 4B, transducer 19 may also be configured with an electronic focusing array 24 in combination with one or more transduction elements 26 to facilitate increased flexibility in treating ROI 12. Focusing array 24 may be configured as an array of electronic apertures that may be operated by a variety of phases via variable electronic time delays, for example, T1, T2, T3 1. By the term "operated," the electronic apertures of array 24 may be manipulated, driven, used, and/or configured to produce and/or deliver energy in a manner corresponding to the phase variation caused by the electronic time delay. For example, these phase variations may be used to deliver defocused beams, planar beams, and/or focused beams, each of which may be used in combination to achieve different physiological effects in ROI 12.

In various embodiments, transduction elements 26 may be configured to be concave, convex, and/or planar. For example, in the embodiment illustrated in FIG. 4A, transduction elements 26A and 26B are configured to be concave in order to provide focused energy for treatment within at least a portion of ROI 12. Additional embodiments are disclosed in U.S. patent application Ser. No. 10/944,500, entitled "System and Method for Variable Depth Ultrasound Treatment," incorporated herein by reference in its entirety.

In another embodiment, as illustrated in FIG. 4B, transduction elements 26A and 26B may be configured to be substantially flat in order to provide substantially uniform energy to RO 12. While FIGS. 4A and 4I illustrate embodiments with transduction elements 26 configured as concave and substantially flat, respectively, transduction elements 26 may be configured to be concave, convex, and/or substantially flat. In addition, transduction elements 26 may be configured to be any combination of concave, convex, and/or substantially flat structures. For example, a first transduction element 26 may be configured to be concave, while a second transduction element 26 may be configured to be substantially flat.

Moreover, transduction element 26 can be any distance from the patient's skin. In that regard, it can be far away from the skin disposed within a long transducer or it can be just a few millimeters from the surface of the patient's skin. In certain embodiments, the transduction element 26 can be positioned closer to the surface of a patient's skin when emitting ultrasound at high frequencies. Moreover, both three and two dimensional arrays of elements can be used in the present invention.

Figure 4C:
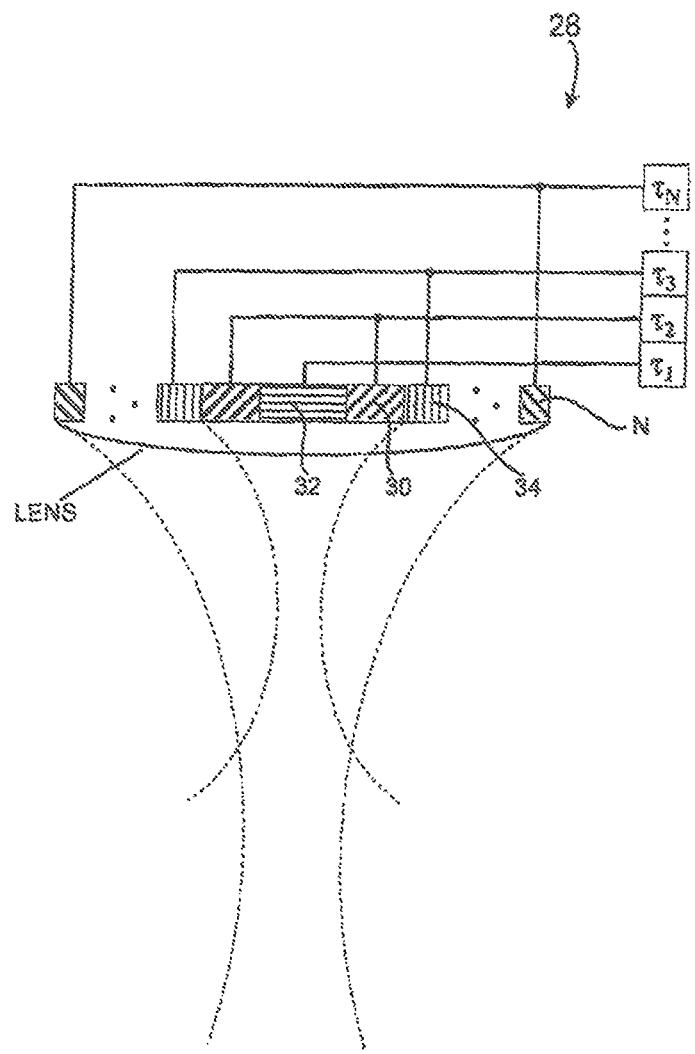
Figure 4D:
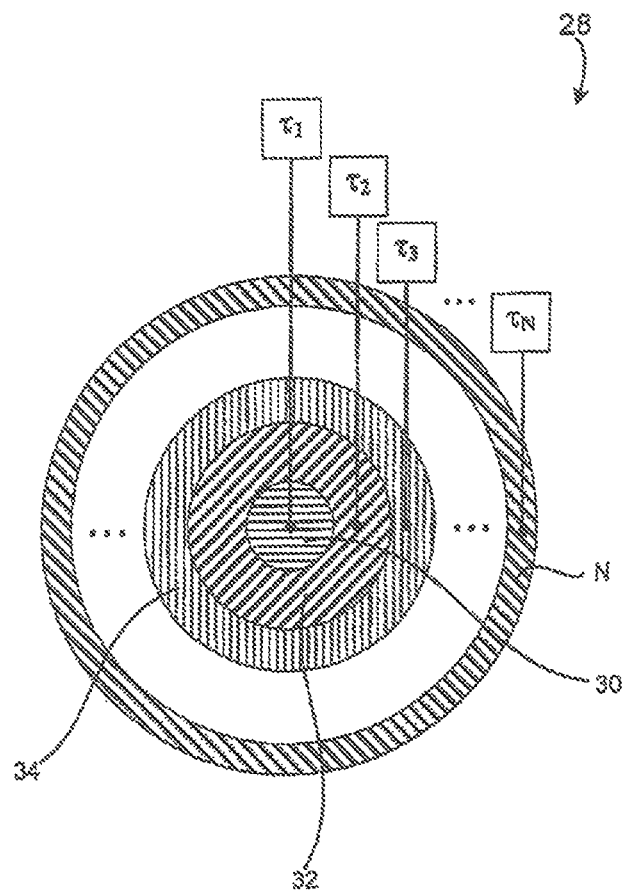

With reference to FIGS. 4C and 4D, transducer 19 may also be configured as an annular array to provide planar, focused and/or defocused acoustical energy. For example, in an embodiment, an annular array 28 may comprise a plurality of rings 30, 32, 34 to N. Rings 30, 32, 34 to N may be mechanically and electrically isolated into a set of individual elements, and may create planar, focused, or defocused waves. For example, such waves can be centered on-axis, such as by methods of adjusting corresponding transmit and/or receive delays, T1, T2, T3 . . . TN. An electronic focus may be suitably moved along various depth positions, and may enable variable strength or beam tightness, while an electronic defocus may have varying amounts of defocusing. In an embodiment, a lens and/or convex or concave shaped annular array 28 may also be provided to aid focusing or defocusing such that any time differential delays can be reduced. Movement of annular array 28 in one, two or three-dimensions, or along any path, such as through use of probes and/or any conventional robotic arm mechanisms, may be implemented to scan and/or treat a volume or any corresponding space within ROI 12.

Figure 4E:
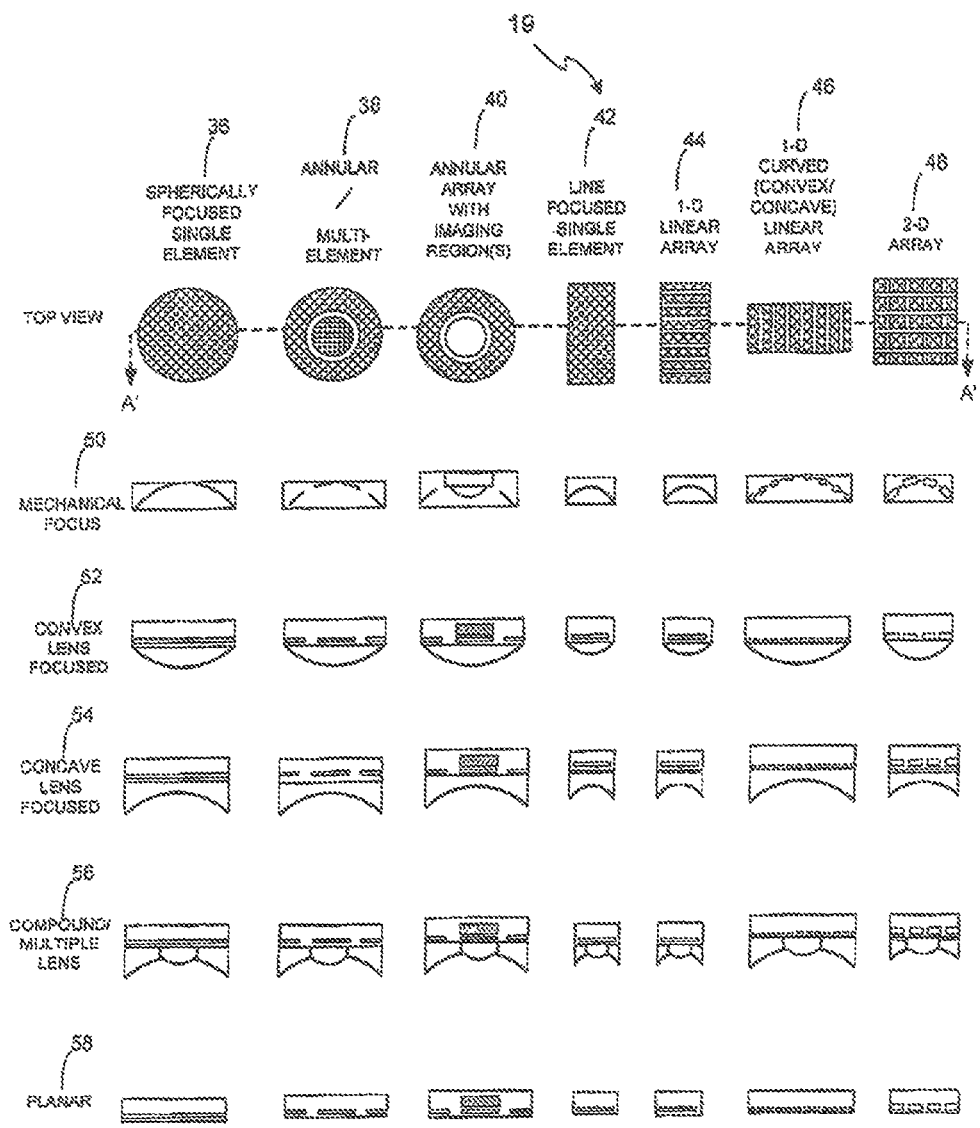

With reference to FIG. 4E, another embodiment of a transducer 19 can be configured to comprise a spherically focused single element 36, annular/multi-element 38, annular with imaging region(s) 40, line-focused single element 42, 1-D linear array 44, 1-D curved (convex/concave) linear array 46, and/or 2-D array 48, combined with mechanical focus 50, convex lens focus 52, concave lens focus 54, compound/multiple lens focused 56, and/or planar array form 58 to achieve focused, unfocused, or defocused sound fields for at least one of imaging and therapy.

Transducer 19 may further comprise a reflective surface, tip, or area at the end of the transducer 19 that emits ultrasound energy. This reflective surface may enhance, magnify, or otherwise change ultrasound energy emitted from system 14.

In various embodiments, a probe 18 may be suitably controlled and operated in various manners by control system 20 as illustrated in FIGS. 2, 3 and 5A-5C which processes and sends one or more images obtained by transducer 19 to display 22. In the embodiment illustrated in FIGS. 5A-5C: control system 20 may be capable of coordination and control of the entire treatment process to achieve the desired effect on tissue within ROI 12. For example, in an embodiment, control system 20 may comprise power source components 60, sensing and monitoring components 62, cooling and coupling controls 64, and/or processing and control logic components 66. Control system 20 may be configured and optimized in a variety of ways with more or less subsystems and components to implement the system 14 for controlled targeting of the desired tissue in ROI 12.

For example, in various embodiments of power sourcing components 60, control system 20 may comprise one or more direct current (DC) power supplies 68 capable of providing electrical energy for the entire control system 20, including power required by a transducer electronic amplifier/driver 70. A DC current sense device 72 may also be provided to confirm the level of power entering amplifiers/drivers 70 for safety and monitoring purposes, among others.

In an embodiment, amplifiers/drivers 70 may comprise multi-channel or single channel power amplifiers and/or drivers. In an embodiment for transducer array configurations, amplifiers/drivers 70 may also be configured with a beamformer to facilitate array focusing. In various embodiments, a beamformer may be electrically excited by an oscillator/digitally controlled waveform synthesizer 74 with related switching logic.

Power sourcing components 60 may also comprise various filtering configurations 76. For example, switchable harmonic filters and/or matching may be used at the output of amplifier/driver 70 to increase the drive efficiency and effectiveness. Power detection components 78 may also be included to confirm appropriate operation and calibration. For example, electric power and other energy detection components 78 may be used to monitor the amount of power entering probe 18.

Various sensing and monitoring components 62 may also be suitably implemented within control system 20. For example, in an embodiment, monitoring, sensing, and interface control components 80 may be capable of operating with various motion detection systems implemented within probe 18, to receive and process information such as acoustic or other spatial and temporal information from ROI 12. Sensing and monitoring components 62 may also comprise various controls, interfacing, and switches 82 and/or power detectors 78. Such sensing and monitoring components 62 may facilitate open-loop and/or closed-loop feedback systems within treatment system 14.

In an embodiment, sensing and monitoring components 62 may further comprise a sensor that may be connected to an audio or visual alarm system to prevent overuse of system 14. In this embodiment, the sensor may be capable of sensing the amount of energy transferred to the skin, and/or the time that system 14 has been actively emitting energy. When a certain time or temperature threshold has been reached, the alarm may sound an audible alarm, or cause a visual indicator to activate to alert the user that a threshold has been reached. This may prevent overuse of the system 14. In an embodiment, the sensor may be operatively connected to control system 20 and force control system 20, to stop emitting ultrasound energy from transducer 19.

In an embodiment, a cooling/coupling control system 84 may be provided, and may be capable of removing waste heat from probe 18. Furthermore the cooling/coupling control system 84 may be capable of providing a controlled temperature at the superficial tissue interface and deeper into tissue, and/or provide acoustic coupling from probe 18 to ROI 12. Such cooling/coupling control systems 84 can also be capable of operating in both open-loop and/or closed-loop feedback arrangements with various coupling and feedback components.

Additionally, in various embodiments, an control system 20 may further comprise a system processor and various digital control logic 86, such as one or more of microcontrollers, microprocessors, field-programmable gate arrays, computer boards, and associated components, including firmware and control software 88, which may be capable of interfacing with user controls and interfacing circuits as well as input/output circuits and systems for communications, displays, interfacing, storage, documentation, and other useful functions. System software 88 may be capable of controlling all initialization, timing, level setting, monitoring, safety monitoring, and all other system functions required to accomplish user-defined treatment objectives. Further, various control switches 90 may also be suitably configured to control operation.

Figure 5A:
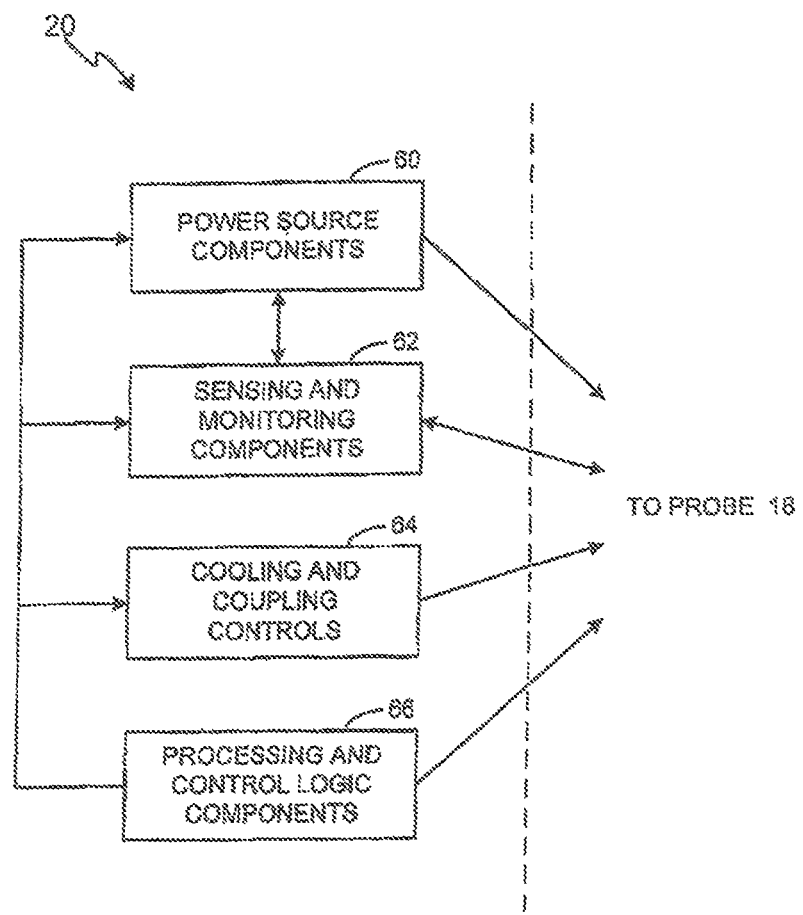
FIGS. 5A, 5B, and 5C illustrate block diagrams of a control system used in a system in accordance with various embodiments of the present invention.
Figure 5B:
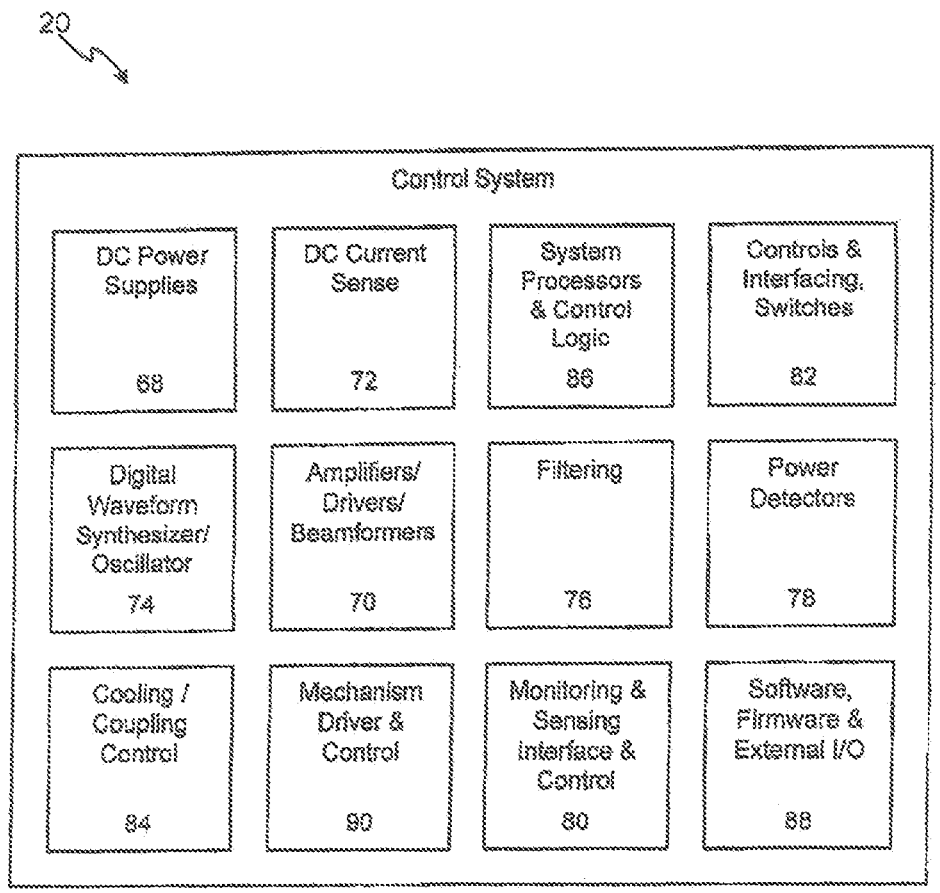
Figure 5C:
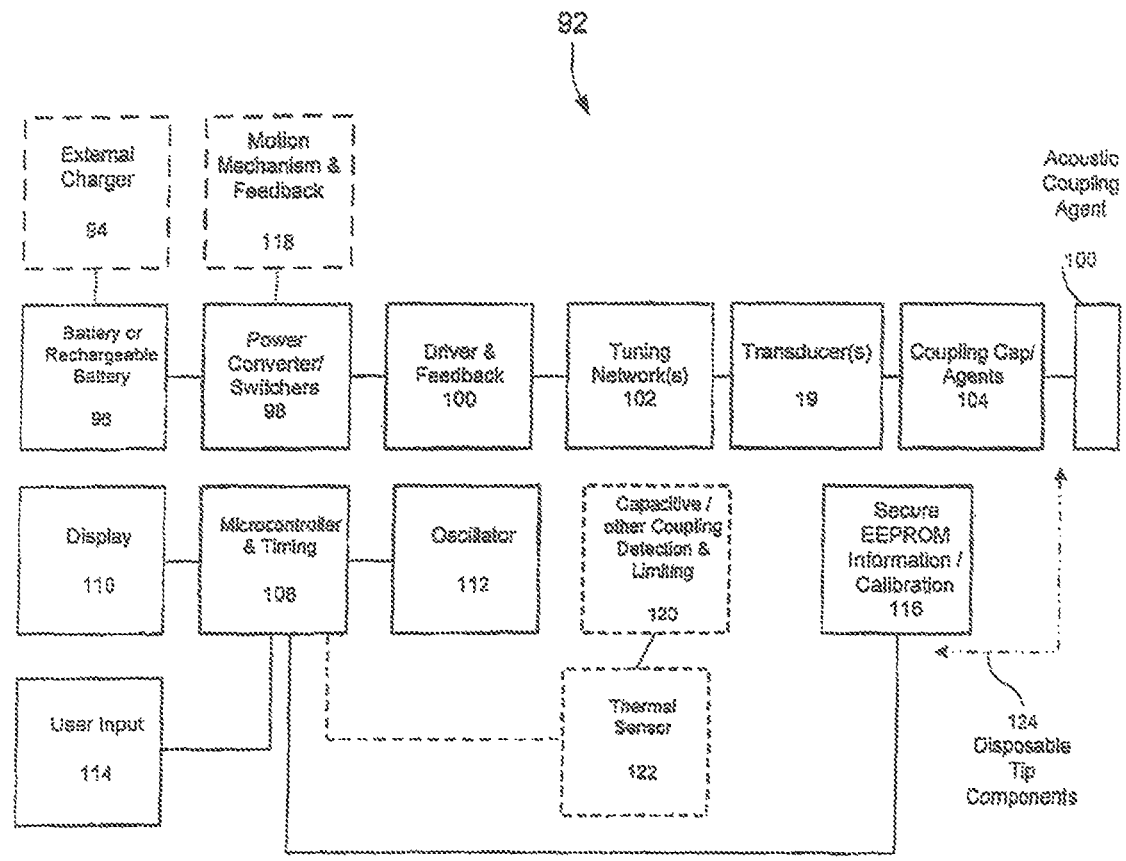

With reference to FIG. 5C, in various embodiments, a transducer 19 may be controlled and operated in various manners by a hand-held format control system 92. An external battery charger 94 can be used with rechargeable-type batteries 96 or the batteries can be single-use disposable types, such as AA-sized cells, Power converters 98 produce voltages suitable for powering a driver/feedback circuit 100 with tuning network 102 driving transducer 19 which is coupled to the patient via one or more acoustic coupling caps 104. Cap 104 can be composed of at least one of a solid media, semi-solid e.g. gelatinous media, and/or liquid media equivalent to an acoustic coupling agent (contained within a housing). Cap 104 is coupled to the patient with an acoustic coupling agent 106. In addition, a microcontroller and timing circuits 108 with associated software and algorithms provide control and user interfacing via a display 110, oscillator 112, and other input/output controls 114 such as switches and audio devices. A storage element 116, such as an Electrically Erasable Programmable Read-Only Memory ("EEPROM"), secure EEPROM, tamper-proof EEPROM, or similar device holds calibration and usage data. A motion mechanism with feedback 118 can be suitably controlled to scan the transducer 19, if desirable, in a line or two-dimensional pattern and/or with variable depth. Other feedback controls comprise a capacitive, acoustic, or other coupling detection means and/or limiting controls 120 and thermal sensor 122. A combination of the secure EEPROM with at least one of coupling caps 104, transducer 19, thermal sensor 122, coupling detectors, or tuning network. Finally, a transducer can further comprise a disposable tip 124 that can be disposed of after contacting a patient and replaced for sanitary reasons.

With reference again to FIGS. 2, 3, and 5, in various embodiments, a system 14 also may comprise display 22 capable of providing images of ROI 12 in certain embodiments where ultrasound energy may be emitted from transducer 19 in a manner suitable for imaging. In an embodiment, display 22 is a computer monitor. Display 22 may be capable of enabling the user to facilitate localization of the treatment area and surrounding structures, e.g., identification of subcutaneous tissue and/or internal organs. In an alternative embodiment, the user may know the location of the specific target below a skin surface, which is to be treated. After localization, ultrasound energy is delivered at a depth, distribution, timing, and energy level to achieve the desired effect within ROI 12. Before, during and/or after delivery of ultrasound energy, monitoring of the treatment area and surrounding structures may be conducted to further plan and assess the results and/or provide feedback to control system 20, and to a system operator via display 22. In an embodiment, localization may be facilitated through ultrasound imaging that may be used to define the position of a target within ROI 12.

In various embodiments, for ultrasound energy delivery, transducer 19 may be mechanically and/or electronically scanned to place treatment zones over an extended area in ROI 12. A treatment depth may be adjusted between a range of approximately 1 to 30 millimeters, or any other depth described herein. Such delivery of energy may occur through imaging of the target, within ROI 12 and then applying ultrasound energy at known depths over an extended area without initial or ongoing imaging.

In various embodiments, the ultrasound beam from transducer 19 may be spatially and/or temporally controlled at least in part by changing the spatial parameters of transducer 19, such as the placement, distance, treatment depth and transducer 19 structure, as well as by changing the temporal parameters of transducer 19, such as the frequency, drive amplitude, and timing, with such control handled via control system 20. Such spatial and temporal parameters may also be suitably monitored and/or utilized in open-loop and/or closed-loop feedback systems within ultrasound system 14.

Finally, it should be noted that while this disclosure is directed primarily to using ultrasound energy to conduct procedures non-invasively, that the method and system described above can also utilize energy such as ultrasound energy to assist in invasive procedures. For example, ultrasound energy can be used to ablate tissues during an invasive procedure. In this regard, ultrasound energy can be used for invasive and minimally invasive procedures.

The present invention has been described herein with reference to various embodiments. However, those skilled in the art will recognize that changes and modifications may be made to any of the various embodiments without departing from the scope of the invention. For example, the various operational steps, as well as the components for carrying out the operational steps, may be implemented in alternate ways depending upon the particular application or in consideration of any number of cost functions associated with the operation of the system, for example, various of the steps may be deleted, modified, or combined with other steps.

Further, it should be noted that while the methods and systems for ultrasound treatment, as described herein, are suitable for use by a medical practitioner proximate the patient, the system can also be accessed remotely, for example, the medical practitioner can view through a remote display having imaging information transmitted in various manners of communication, such as by satellite/wireless or by wired connections such as IP or digital cable networks and the like, and can direct a local practitioner as to the suitable placement for the transducer. Moreover, while the various embodiments may comprise non-invasive configurations, systems and methods can also be configured for at least some level of invasive treatment applications.

The various embodiments, as disclosed and illustrated herein, are not to be considered in a limiting sense as numerous variations are possible. The subject matter of the various embodiments of the invention includes any and all novel and non-obvious combinations and sub combinations of the various elements, features, functions and/or properties disclosed herein. These and other changes or modifications are intended to be included within the scope of the present invention, as set forth in the following claims.

The invention claimed is:

1. A method of providing non-invasive ultrasound treatment of tissue, the method comprising:
    coupling an acoustic source to a region of interest comprising a surface and subcutaneous tissue;
    providing a first acoustic energy into the subcutaneous tissue of the region of interest;
    creating thermal bubbles in an outer portion of the region of interest;
    forming a boundary comprising the thermal bubbles in the outer portion of the region of interest, thereby surrounding an inner portion of the region of interest with the boundary;
    providing a second acoustic energy into the inner portion of the region of interest; and
    containing the second acoustic energy within the boundary;
    thereby protecting tissue outside of the inner portion from the second acoustic energy.

2. The method according to claim 1, further comprising reflecting a portion of the second acoustic energy off of at least one of the thermal bubbles in the boundary and directing a reflected portion of the second acoustic energy into the inner portion of the region of interest.

3. The method according to claim 2, further comprising directing the reflected portion of the second acoustic energy away from the tissue outside of the inner portion.

4. The method according to claim 2, further comprising scattering the reflected portion of the second acoustic energy into the inner portion of the region of interest.

5. The method according to claim 2, further comprising concentrating the second acoustic energy into the inner portion of the region of interest.

6. The method according to claim 1, wherein the second acoustic energy stimulates a bio-effect in the inner portion of the region of interest.

7. The method according to claim 6, wherein the bio-effect in the inner portion of the region of interest is reducing a volume of the subcutaneous tissue.

8. The method according to claim 6, the bio-effect in the inner portion of the region of interest is enhancing formation of collagen in the region of interest.

9. The method according to claim 1, wherein the tissue outside of the region of interest comprises an internal organ.

10. A method of cosmetic enhancement, the method comprising:
    coupling at least one source to a region of interest;
    directing a first energy from the at least one source into the region of interest;
    creating a boundary comprising a plurality of thermal bubbles in a non-target region with the first energy, thereby surrounding a target region in the region of interest with the boundary; and
    directing a second energy from the at least one source inside the boundary and into the target region in the region of interest.

11. The method according to claim 10, further comprising reflecting a portion of the second energy off of at least one of the thermal bubbles in the boundary and directing a reflected portion of the second energy into the target region.

12. The method according to claim 11, further comprising concentrating the second energy into the target region.

13. The method according to claim 10, wherein the second energy stimulates a bio-effect in at least a portion of the target region.

14. The method according to claim 13, wherein the bio-effect in at least a portion of the target region is reducing a volume of tissue in the target region.

15. The method according to claim 13, wherein the bio-effect in at least a portion of the target region is enhancing formation of collagen in the target region.

16. The method according to claim 10, wherein the at least one source comprises an ultrasound source and a pulsed laser.

17. The method according to claim 10, wherein the first energy is ultrasound energy and the second energy is photon-based energy.

18. The method according to claim 10, wherein the first energy is ultrasound energy and the second energy is ultrasound energy.

19. The method according to claim 10, wherein tissue in the non-target region comprises an internal organ.

* * * * *